US009642849B2

(12) United States Patent
Torup et al.

(10) Patent No.: US 9,642,849 B2
(45) Date of Patent: May 9, 2017

(54) NALMEFENE FOR REDUCTION OF ALCOHOL CONSUMPTION IN SPECIFIC TARGET POPULATIONS

(71) Applicant: H. Lundbeck A/S, Valby (DK)

(72) Inventors: Lars Torup, Væløse (DK); Afsaneh Abbariki, Holte (DK); Anna Bladström, Lund (SE); Christine Persson, Lund (SE); Didier Meulien, Boulogne Billancourt (FR); Per Sørensen, København Ø (DK); Thomas Jon Jensen, Virum (DK); Jette Buch Østergaard, København N (DK)

(73) Assignee: H. LUNDBECK A/S, Valby (DK)

( * ) Notice: Subject to any disclaimer, the term of this patent is extended or adjusted under 35 U.S.C. 154(b) by 0 days.

(21) Appl. No.: 15/093,097

(22) Filed: Apr. 7, 2016

(65) Prior Publication Data
US 2016/0375007 A1 Dec. 29, 2016

Related U.S. Application Data

(63) Continuation of application No. 13/928,332, filed on Jun. 26, 2013, now abandoned.

(60) Provisional application No. 61/788,810, filed on Mar. 15, 2013, provisional application No. 61/736,740, filed on Dec. 13, 2012, provisional application No. 61/721,539, filed on Nov. 2, 2012, provisional application No. 61/664,804, filed on Jun. 27, 2012.

(51) Int. Cl.
*A61K 31/485* (2006.01)
*A61K 9/00* (2006.01)

(52) U.S. Cl.
CPC .......... *A61K 31/485* (2013.01); *A61K 9/0053* (2013.01)

(58) Field of Classification Search
CPC ............................. A61K 31/485; A61K 9/0085
See application file for complete search history.

(56) References Cited

U.S. PATENT DOCUMENTS

| 3,814,768 A | 6/1974 | Fishman | |
|---|---|---|---|
| 4,535,157 A | 8/1985 | Meltzer et al. | |
| 5,086,058 A * | 2/1992 | Sinclair | A61K 31/485 514/282 |
| 8,530,495 B2 * | 9/2013 | Lopez de Diego | C07D 489/08 514/282 |
| 2014/0005217 A1 | 1/2014 | Torup et al. | |

FOREIGN PATENT DOCUMENTS

| EP | 0140367 | 5/1985 |
|---|---|---|
| WO | WO 03/015783 | 2/2003 |
| WO | WO-2012134410 A1 | 10/2012 |

OTHER PUBLICATIONS

Ciccocioppo et al. (Biol. Psychiatry (2007); 61:4-12).*
Clinical Trials (2010).*
Clinical Trials (2009).*
Starosfa et al (J. psychaitr. Pract (2006) 12(2):80-89).*
Fitzgerald et al., "Weak evidence on nalmefene creates dilemmas for clinicians and poses questions for regulators and researchers," Addiction, 111(8), pp. 1477-1487 (2016).
Naudet et al., "Cost-Effectiveness of Nalmefene: Exaggerated Expectations or Fallacy?" Alcohol and Alcoholism pp. 1-2 (2016).
van den Brink et al., "Efficacy of as-needed nalmefene in alcohol-dependent patients with at least a high drinking risk level: results from a subgroup analysis of two randomised controlled 6-month studies," Alcohol and Alcoholism, 48(5), pp. 570-578 (2013).
van den Brink et al., "Safety and tolerability of as-needed nalmefene in the treatment of alcohol dependence: results from the Phase III clinical programme," Expert Opin. Drug Saf. 14(4) pp. 495-504 (2015).
van den Brink et al., "Long-Term Efficacy, Tolerability, and Safety of Nalmefene in Patients With Alcohol Dependence," Presented at the 16th Congress of the International Society for Biomedical Research on Alcoholism (ISBRA) Sep. 9-12, 2012.
Anton, R.F. et al., (2004) "A Multi-Site Dose Ranging Studying of Nalmefene in the Treatment of Alcohol Dependence," J. Clin. Psychopharmacol. 24(4):421-428.
Anton, R.F. et al., (2006) "Combine Pharmacotherapies and Behavioral Interventions for Alcohol Dependence, The COMBINE Study: A Randomized Controlled Trial," J. Am. Med. Assoc. 295(17):2003-2017.
Clifford, P.R. et al., (2000) "Subject Reactivity Effects and Alcohol Treatment Outcome Research,": J. Stud. Alcohol 61(6):787-793.
ClinicalTrials.gov (2010) "Safety and Efficacy of Nalmefene in Patients with Alcohol Dependence (SENSE)," Clinical Trial Identifier: NCT00811941.
Epstein, E.E. et al., (2005) "Is Alcohol Assessment Therapeutic? Pretreatment Change in Drinking Among Alcohol-Dependent Women," J. Stud. Alcohol 66(3):369-378.
Gastfriend, D.R. et al., (2007) "Reduction in Heavy Driving as a Treatment Outcome in Alcohol Dependence," J. Subst. Abuse Treat. 33:71-80.
Gual, A. et al., (2012) "Esense 2: A Randomised, Double-Blind, Placebo-Controlled Study of Nalmefene, An-Needed Use in Alcohol Dependent Patients," Presented at the 35th Annual RSA Scientific Meeting, San Francisco, CA, USA (2 pages).
Gual, A. et al., (2012) "Randomised, Double-Blind, Placebo-Controlled Study of Nalmefene in Patients with Alcohol Dependence," Presented at the 16th Congress of the Int'l Society for Biomedical Res. on Alcoholism (ISBRA) (2 pages).

(Continued)

*Primary Examiner* — Shirley V Gembeh
(74) *Attorney, Agent, or Firm* — Wilmer Cutler Pickering Hale and Dorr LLP

(57) ABSTRACT

The present invention relates to nalmefene for use in the reduction of alcohol consumption in a patient with alcohol dependence who has a high drinking risk level. The present invention also relates to nalmefene for use in the reduction of alcohol consumption in a patient with alcohol dependence who maintains a high DRL after an observation period following initial assessment.

35 Claims, 12 Drawing Sheets

(56) References Cited

OTHER PUBLICATIONS

Gual, A. et al., (2013) "A Randomised, Double-Blind, Placebo-Controlled, Efficacy Study of Nalmefene, As-Needed Use, in Patients with Alcohol Dependence," Eur. Neuropsychopharmacol. 23(11):1432-1442.
Gual, A. et al., (2013) "Demographics and Baseline Characteristics of the Nalmefene Phase 3 Programme Study Population," 20th Wonca World Conference, Prague, Czech Republic (1 page).
Gual, A. et al., (2013) "Efficacy of Nalmefene As-Needed in Alcohol Dependent Patients with High Drinking Risk Level: Subgroup Analysis of Two Randomised Controlled Studies," 20th Wonca World Conference, Prague, Czech Republic (1 page).
International Search Report PCT/EP2013/063461 (WO 2014/001427) (2013) (4 pages).
Karhuvaara, S. et al., (2007) "Targeted Nalmefene with Simple Medical Management in the Treatment of Heavy Drinkers: A Randomized Double-Blind Placebo-Controlled Multicenter Study," Alcohol Clin. Exp. Res. 31(7):1179-1187.
Litten, R.Z. et al., (2012) "A Double-Blind, Placebo-Controlled Trial to Assess the Efficacy of Quetiapine Fumarate XR in Very Heavy-Drinking Alcohol-Dependent Patients," Alcohol Clin. Exp. Res. 36(3):406-416.
Mann, K. et al., (2012) "A New Treatment Paradigm: Nalmefene Reduces Alcohol Consumption in Patients with Alcohol Dependence," Presented at the 16th Congress of the Int'l Society for Biomedical Res. on Alcoholism (ISBRA) (1 page).
Mann, K. et al., (2012) "Shifting the Paradigm: Reduction of Alcohol Consumption in Alcohol Dependent Patients—A Randomised, Double-Blind, Placebo-Controlled Study of Nalmefene, As-Needed Use," Presented at the 20th European Congress of Psychiatry, Prague, Czech Republic (1 page).
Mann, K. et al., (2012) "Shifting the Pradigm: Esense 1—A Ranomised, Double-Blind, Placebo-Controlled Study of Nalmefene, As-Needed Use in Alcohol Dependent Patients," Presented at the 35th Annual RSA Scientific Meeting, San Francisco, CA, USA (2 pages).
Mann, K. et al., (2013) "Extending the Treatment Options in Alcohol Dependence: A Randomized Controlled Study of As-Needed Nalmefene," Biological Psychiatry 73(8):706-713.
Mann, K. et al., (2013) "Long-Term Efficacy of Nalmefene As-Needed in Alcohol Dependent Patients with High Drinking Risk Levels: Results of a Subgroup Analysis," 36th Annual RSA Scientific Meeting, Orlando, USA (1 page).
Mason, B.J. et al., (1994) "A Double-Blind, Placebo-Controlled Pilot Study to Evaluate the Efficacy and Safety of Oral Nalmefene HCI for Alcohol Dependence," Alcohol. Clin. Exp. Res. 18(5):1162-1167.
Mason, B.J. et al., (1999) "A Double-Blind, Placebo-Controlled Study of Oral Nalmefene for Alcohol Dependence," Arch. Gen. Psychiatry 56(8):719-724.
Sharpe, P.C. (2001) "Biochemical Detection and Monitoring of Alcohol Abuse and Abstinence," Ann. Clin. Biochem. 38:652-664.
Sinclair, J. et al., (2013) "As-Needed Use of Nalmefene in the Treatment of Alcohol Dependence," 36th Annual RSA Scientific Meeting, Orlando, USA (1 page).
Sinclair, J. et al., (2013) "As-Needed Use of Nalmefene in the Treatment of Alcohol Dependence," Presented at the 21st European Congress of Psychiatry, Nice, France (1 page).
Sinclair, J.D. (2001) "Evidence About the Use of Naltrexone and for Difference Ways of Using it in the Treatment of Alcoholism," Alcohol & Alcoholism 36:2-10.
Sobell, M.B. et al., (1992) "Timeline Follow-Back, A Technique for Assessing Self-Reported Alcohol Consumption," Measuring Alcohol Consumption: Psychosocial and Biochemical Methods 41-72.
Starosta, A.N. et al., (2006) "The BRENDA Model: Integrating Psychosocial Treatment and Pharmacotherapy for the Treatment of Alcohol Use Disorders," J. Psychiatr. Pract. 12(2):80-89.
van den Brink, W. et al., (2012) "Long-Term Efficacy, Tolerability and Safety of Nalmefene As-Needed in Alcohol-Dependence: A Randomised, Double-Blind, Placebo-Controlled Study," Presented at the 35th Annual RSA Scientific Meeting, San Francisco, CA, USA (2 pages).
van den Brink, W. et al., (2013) "Efficacy of Nalmefene As-Needed in Alcohol Dependent Patients with High Drinking Risk Level: Subgroup Analysis of Two Randomised Controlled Studies," 36th Annual RSA Scientific Meeting, Orlando, USA (1 page).
van den Brink, W. et al., (2013) "Esense 1—Randomised Controlled 6-Month Study of As-Needed Nalmefene: Subgroup Analysis of Alcohol Dependent Patients with High Drinking Risk Level," Presented at the 21st European Congress of Psychiatry, Nice, France (1 page).
van den Brink, W. et al., (2013) "Esense 2—Randomised Controlled 6-Month Study of As-Needed Nalmefene: Subgroup Analysis of Alcohol Dependent Patients with High Drinking Risk Level," Presented at the 21st European Congress of Psychiatry Nice, France (1 page).
van den Brink, W. et al., (2013) "Long-Term Efficacy of Nalmefene As-Needed in Alcohol Dependent Patients with High Drinking Risk Levels: Results of a Subgroup Analysis," Presented at the 21st European Congress of Psychiatry, Nice, France (1 page).
van den Brink, W. et al., (2014) "Long-Term Efficacy, Tolerability and Safety of Nalmefene As-Needed in Patients with Alcohol Dependence: A 1-Year, Randomised Controlled Study," J. Psychopharmacol. 28(8):733-744.
World Health Organization (2000) "International Guide for Monitoring Alcohol Consumption and Related Harm," Department of Mental Health and Substance Dependence Noncommunicable Diseases and Mental Health Cluster 1-62.
World Health Organization (2000) "International Guide for Monitoring Alcohol Consumption and Related Harm," Department of Mental Health and Substance Dependence Noncommunicable Diseases and Mental Health Cluster 63-130.
World Health Organization (2000) "International Guide for Monitoring Alcohol Consumption and Related Harm," Department of Mental Health and Substance Dependence Noncommunicable Diseases and Mental Health Cluster 131-193.
World Health Organization (2011) "Global Status Report on Alcohol and Health" 1-58, 273-286.
Written Opinion of the International Searching Authority PCT/EP2013/063461 (WO 2014/001427) (2013) (4 pages).
van den Brink et al., "Long-term efficacy, tolerability and safety of nalmefene as-needed in patients with alcohol dependence: A 1-year, randomised controlled study," *Journal of Psychopharmacology*, 28(8) pp. 733-744 (2014).
"Lundbeck receives positive opinion for approval of Selincro (nalmefene) in the European Union", Lundbeck Press Release, Dec. 14, 2012, retrieved from http://investor.lundbeck.com/releasedetail.cfm?ReleaseID=726936 on Jan. 20, 2017, consisting of 4 pages.
"Biotie: Selincro (nalmefene) receives European marketing authorization", Biotie Therapies Corp.—Stock Exchange Release, Feb. 28, 2013, retrieved from http://www.biotie.com/investors/releases/pr-story.aspx?ResultPageURL=http://cws.huginonline.com/B/132030/PR/201302/1681977.xml on Jan. 20, 2017, consisting of 3 pages.
"Lundbeck receives European marketing authorization for Selincro as the first therapy approved for the reduction of alcohol consumption", Lundbeck Corporate Press Release No. 494, Feb. 28, 2013, consisting of 4 pages.
"Selincro (TM) (nalmefene) receives positive opinion for approval in the European Union", Biotie Therapies Corp.—Stock Exchange Release, Dec. 14, 2012, retrieved from http://www.biotie.com/investors/releases/pr-story.aspx?ResultPageURL=http://cws.huginonline.com/B/132030/PR/201212/1665023.xml on Jan. 20, 2017, consisting of 3 pages.
"EPAR Summary for the Public—Selincro (nalmefene)", European Medicines Agency—Science Medicines Health, EMA/826403/2012, EMEA/H/C/002583, Feb. 2013, consisting of 3 pages.
Johnson, et al., "Severity of alcoholism in Indian males: Correlation with age of onset and family history of alcoholism", Indian Journal of Psychiatry, vol. 52, No. 3, pp. 243-249 (2010).

(56) References Cited

OTHER PUBLICATIONS

Turner, et al., "Family History Models of Alcoholism: Age of Onset, Consequences and Dependence", Journal of Studies of Alcohol, vol. 54, No. 2, pp. 164-171 (1993).

Volicer, et al., "Relationship of Family History of Alcoholism to Patterns of Drinking and Physical Dependence in Male Alcoholics", Drug and Alcohol Dependence, vol. 13, No. 3, pp. 215-223 (1984).

"History of Changes and the ClinicalTrials.gov Archive Site," <https://clinicaltrials.gov/ct2/archive/NCT00811941> retrieved Nov. 3, 2016 (1 page).

"History of NCT00811941" <https://clinicaltrials.gov/archive/NCT00811941> retrieved Nov. 3, 2016 (1 page).

Center for Substance Abuse Treatment, "Incorporating Alcohol Pharmacotherapies Into Medical Practice. Treatment Improvement Protocol (TIP) Series 49," HHS Publication No. (SMA) 09-4380. Rockville, MD: Substance Abuse and Mental Health Services Administration, 126 pages (2009).

H. Lundbeck A/S "A 52-week, Randomised, Double-blind, Placebo-controlled, Parallel-group, Safety, Tolerability and Efficacy Study of Nalmefene, as Needed Use, in Patients With Alcohol Dependence" <http://clinicaltrials.gov/archive/NCT00811941/2011_08_09> retrieved Dec. 14, 2014 (3 pages) Clinical Trials 2011 version, Before (Updated 2011_08_09).

H. Lundbeck A/S "A 52-week, Randomised, Double-blind, Placebo-controlled, Parallel-group, Safety, Tolerability and Efficacy Study of Nalmefene, as Needed Use, in Patients With Alcohol Dependence" <http://clinicaltrials.gov/archive/NCT00811941/2013_08_06/changes> retrieved Dec. 14, 2014 (172 pages) Clinical Trials 2013 mark up over 2011 version.

Levin, "Lundbeck receives European marketing authorization for Selincro as the first therapy approved for the reduction of alcohol consumption," <http://www.fiercebiotech.com/biotech/lundbeck-receives-european-marketing-authorization-for-selincro-as-first-therapy-approved> Feb. 28, 2013, retrieved Nov. 17, 2016 (7 pages).

* cited by examiner

NALMEFENE FOR REDUCTION OF ALCOHOL CONSUMPTION IN SPECIFIC TARGET POPULATIONS

CROSS-REFERENCE TO RELATED APPLICATIONS

This application is a continuation of, and claims priority to, U.S. patent application Ser. No. 13/928,332, filed Jun. 26, 2013, which application claims priority to U.S. Patent Applns. Ser. No. 61/788,810, filed Mar. 15, 2013, 61/736,740, filed Dec. 13, 2012, 61/721,539 filed Nov. 2, 2012, and 61/664,804, filed Jun. 27, 2012.

FIELD OF THE INVENTION

The present invention relates to nalmefene for use in the reduction of alcohol consumption in a patient with alcohol dependence who has a high drinking risk level. The present invention also relates to nalmefene for use in the reduction of alcohol consumption in a patient with alcohol dependence who maintains a high DRL after an observation period following initial assessment.

BACKGROUND OF THE INVENTION

Nalmefene [17-(cyclopropylmethyl)-4,S~alpha-epoxy-6-methylenemorphinan-3,14-diol] has the following general formula:

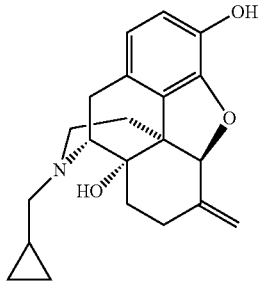

and can be prepared using methods that are well known in the art e.g. starting by manufacturing of naltrexone from noroxymorphone as described in WO 2012/059103 and subsequently manufacturing nalmefene from naltrexone e.g. by the Wittig reaction as described in WO 2010/136039. The entire contents of each of WO 2012/059103 and WO 2010/136039 are incorporated herein by reference.

Nalmefene is a known opioid system modulator, with a distinct μ, δ, and κ receptor profile, which can inhibit pharmacological effects of both administered opioid agonists and endogenous agonists derived from the opioid system. The clinical usefulness of nalmefene comes from its ability to promptly and selectively reverse the effects of these opioid agonists.

Nalmefene has primarily been developed for use in the management of alcohol dependence. A double-blind, placebo-controlled study has shown good effect of 20 to 80 mg daily oral dosing of nalmefene (Mason et al., Arch. Gen. Psychiatry, (1999), Vol. 56: 719-724); while another study reported no evidence of superiority of nalmefene over placebo in a study evaluating 5, 20 and 40 mg daily doses of nalmefene (Anton et al., J. Clin. Psychopharmacol., (2004), Vol. 24(4): 421-428). A more recent study, showed good effect of nalmefene over placebo when a dose of 20 mg nalmefene was taken when the patient experienced a craving for alcohol (Karhuvaara et al., Alcohol. Clin. Exp. Res., (2007), Vol. 31(7): 1179-1187).

Based on independent evidence, high levels of alcohol consumption are associated with an increased risk of health-related harm, as well as adverse social consequences. The World Heath Organization (WHO) has defined drinking risk levels (DRLs) based on alcohol consumption in *International Guide for Monitoring Alcohol Consumption and Related Harm*. 2000. World Health Organization, the entire contents of which are incorporated herein by reference. See Table 1.

TABLE 1

WHO Drinking Risk Levels (DRLs) of Alcohol Consumption

| | Total Alcohol Consumption (g/day) | |
|---|---|---|
| DRL | Men | Women |
| Very high risk | >100 | >60 |
| High risk | >60 to 100 | >40 to 60 |
| Medium risk | >40 to 60 | >20 to 40 |
| Low risk | 1 to 40 | 1 to 20 |

Risk levels according to Table 1 can be assessed e.g. by calculating mean daily alcohol consumption in g/day over a month such as over 4 weeks. There is a need for a new treatment for use in reduction of alcohol consumption. Reduction of alcohol consumption is likely to provide benefits associated with decreased risk of health-related harm and decreased number of adverse social consequences.

SUMMARY OF THE INVENTION

The present invention relates to a nalmefene for use in the reduction of alcohol consumption in a patient with alcohol dependence, wherein said use comprises the following steps;
a) identifying a patient with alcohol dependence i) who has a high DRL, and ii) who maintains a high DRL after an observation period following initial assessment, and
b) administering a therapeutically effective amount of nalmefene to the patient identified in step a), wherein said nalmefene is to be administered as needed such as on each day the patient perceives a risk of drinking alcohol, preferably 1-2 hours prior to the anticipated time of drinking.

BRIEF DESCRIPTION OF DRAWINGS

FIGS. 1-12 show the change from baseline in monthly Heavy Drinking days (HDDs) and Total Alcohol Consumption (TAC) (g/day) per study. Results are shown for the Total study population, Patients with a high DRL at baseline, Total study population excluding Early Reducers (ERs) and Patients with a high DRL at baseline and randomization FIGS. 1a-12a show the change from baseline in monthly HDDs. X-axis; time (months); Y-axis: change in HDD.

FIGS. 1b-12b show the change from baseline in monthly TAG (g/day. X-axis: time (months); Y-axis: change in TAC (g/day).

(—□—=placebo, —■—=nalmefene, *=P-value<0.05), "B" denotes baseline, "R" denotes randomization.

Figure 1A:
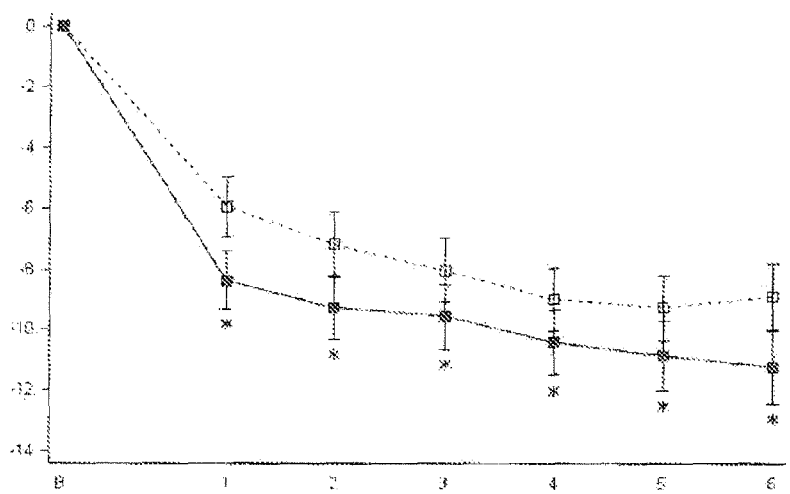

FIG. 1a: Study 12014A, total study population, change in monthly HDD.

Figure 1B:
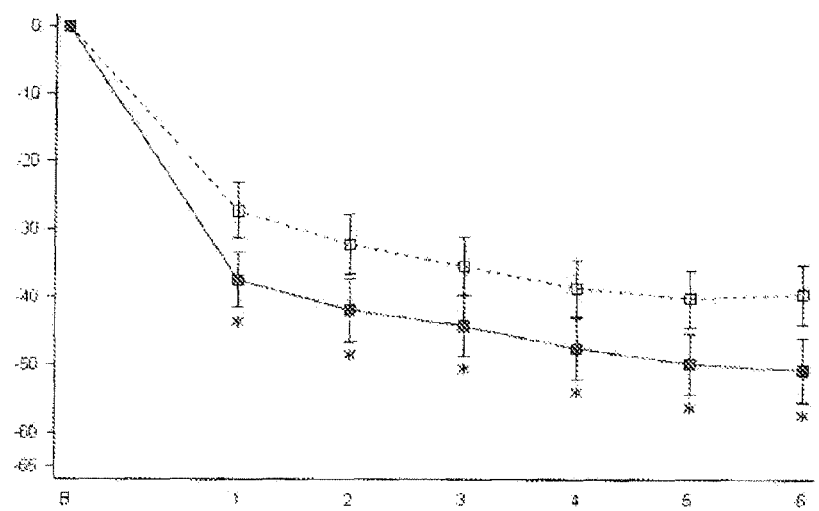

FIG. 1b: Study 12014A, total study population, change in monthly TAC.

Figure 2A:
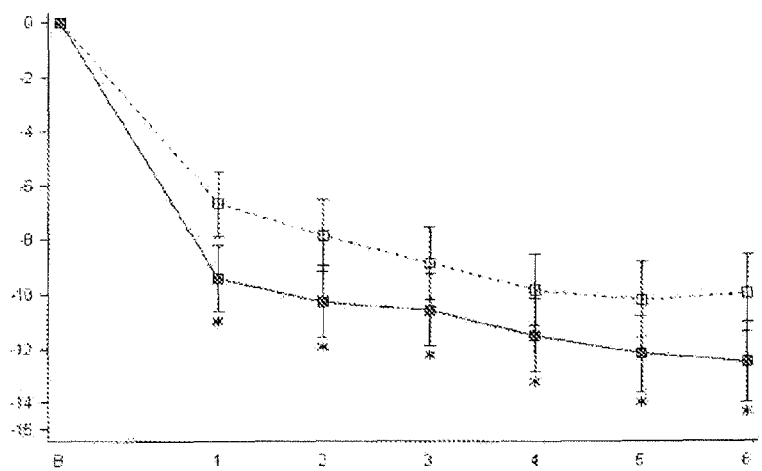

FIG. 2a: Study 12014A, high DRL at baseline, change in monthly HDD.

Figure 2B:
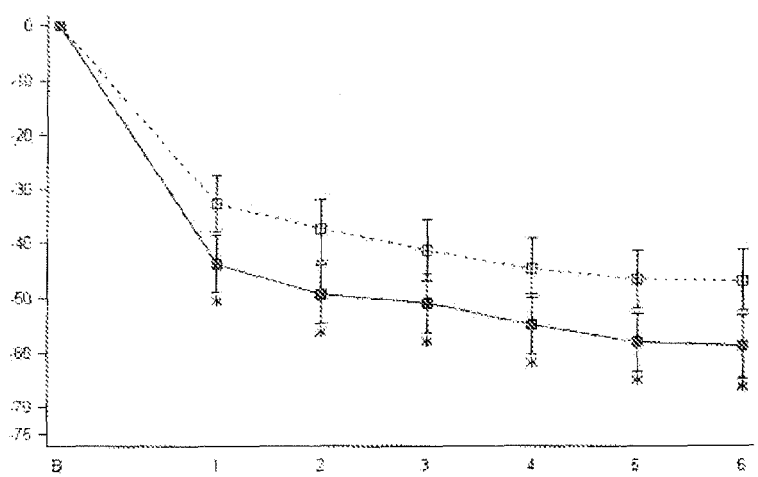

FIG. 2b: Study 12014A, high DRL at baseline, change in monthly TAC.

Figure 3A:
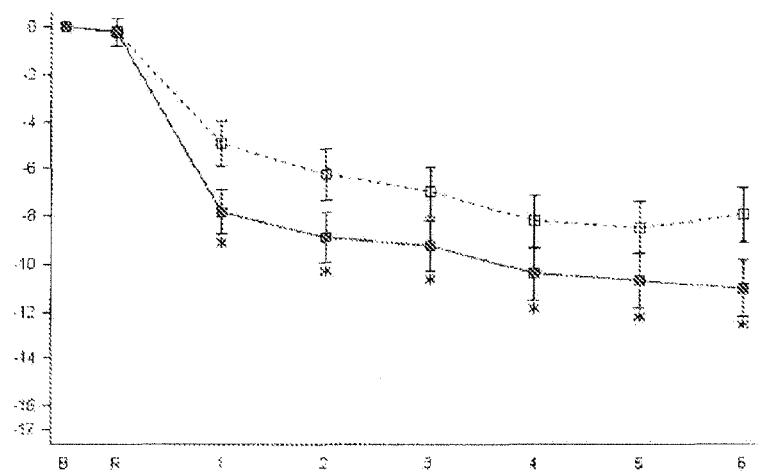

FIG. 3a: Study 12014A, total study population excluding ERs, change in monthly HDD.

Figure 3B:
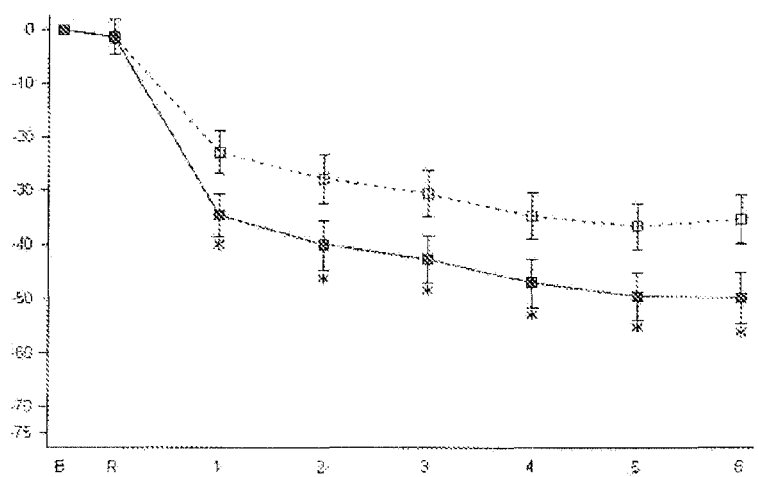

FIG. 3b: Study 12014A, total study population excluding ERs, change in monthly TAG.

Figure 4A:
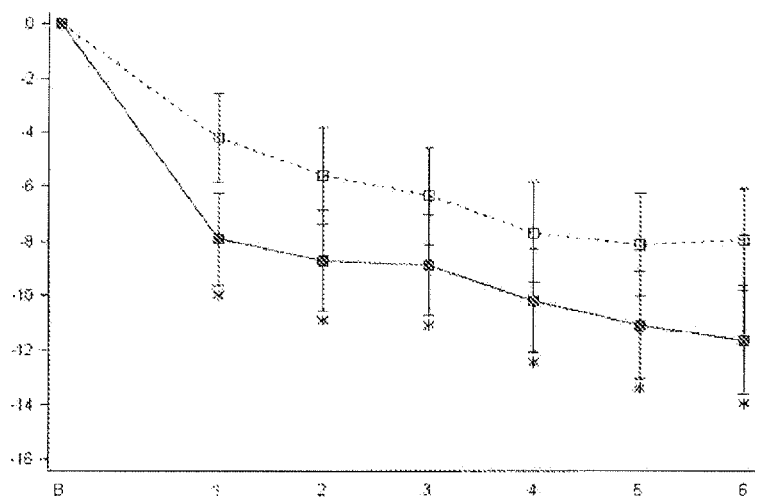

FIG. 4a. Study 12014A, high DRL at baseline and randomization, change in monthly HDD.

Figure 4B:
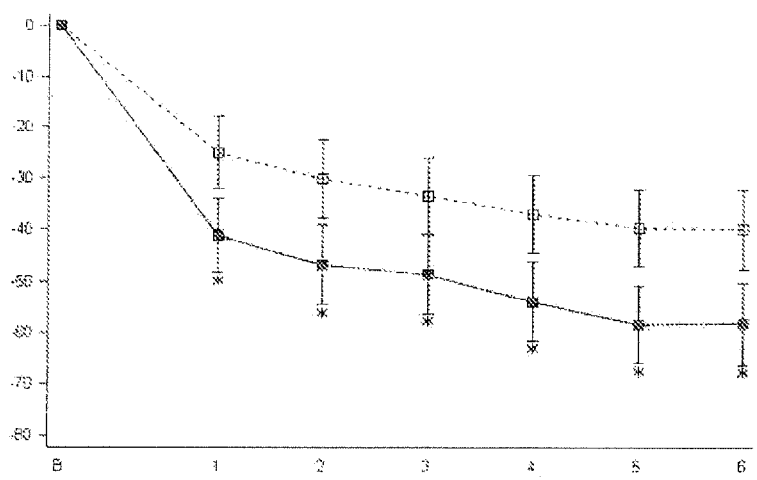

FIG. 4b: Study 12014A, high DRL at baseline and randomization, change in monthly TAC.

Figure 5A:
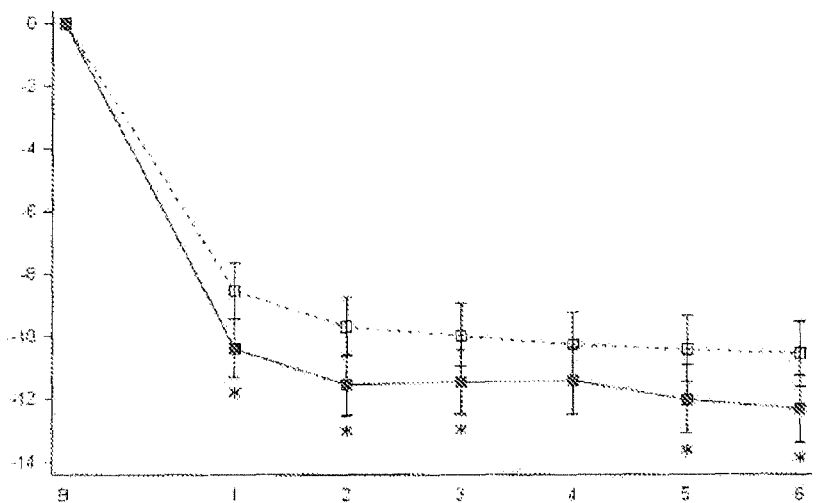

FIG. 5a: Study 12023A, total study population, change in monthly HDD.

Figure 5B:
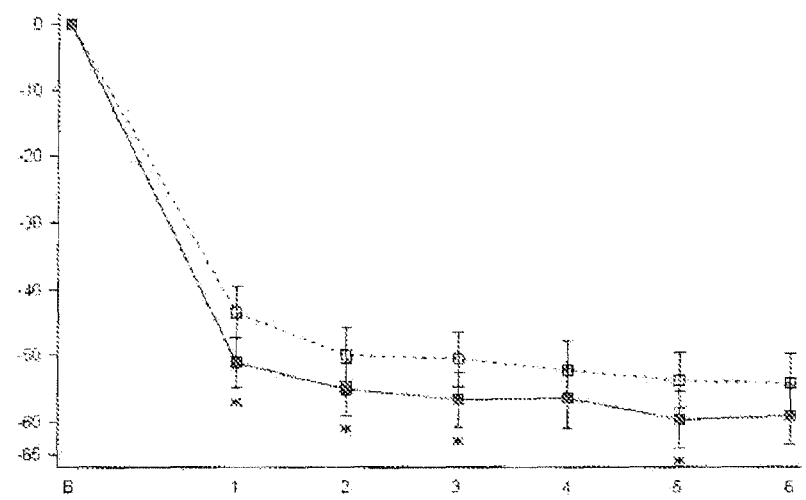

FIG. 5b: Study 12023A, total study population, change in monthly TAC.

Figure 6A:
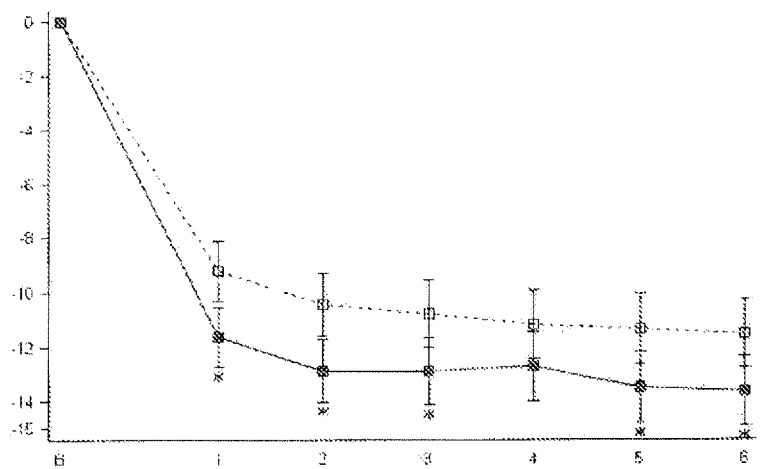

FIG. 6a: Study 12023A, high DRL at baseline, change in monthly HDD.

Figure 6B:
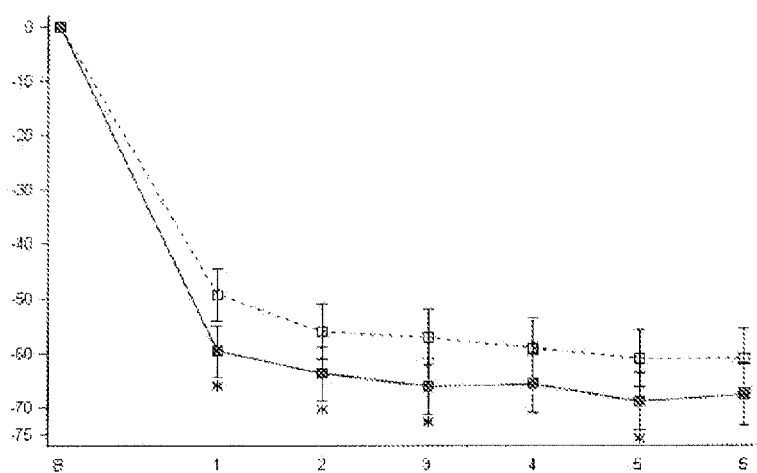

FIG. 6b: Study 12023A, high DRL at baseline, change in monthly TAC.

Figure 7A:
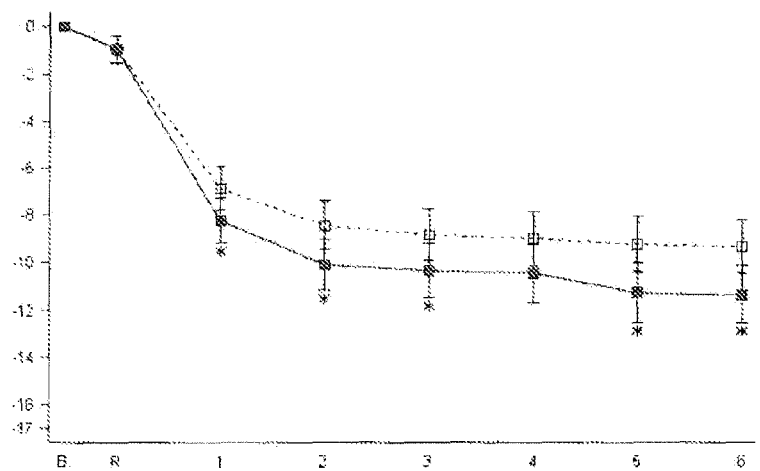

FIG. 7a: Study 12023A, total study population excluding ERs, change in monthly HDD.

Figure 7B:
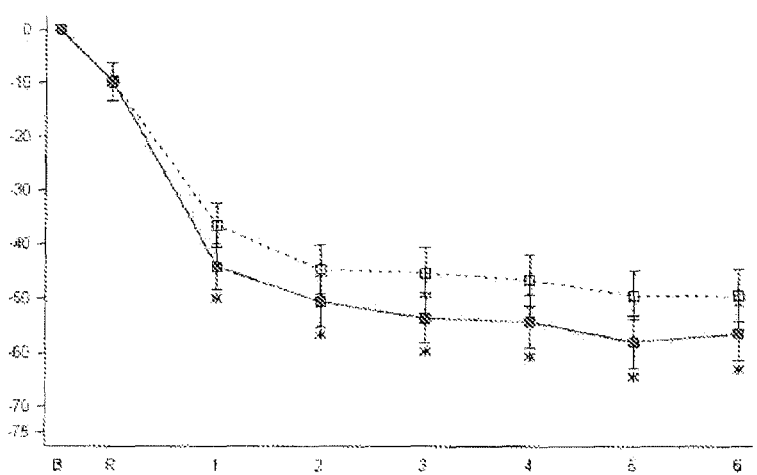

FIG. 7b: Study 12023A, total study population excluding ERs, change in monthly TAC.

Figure 8A:
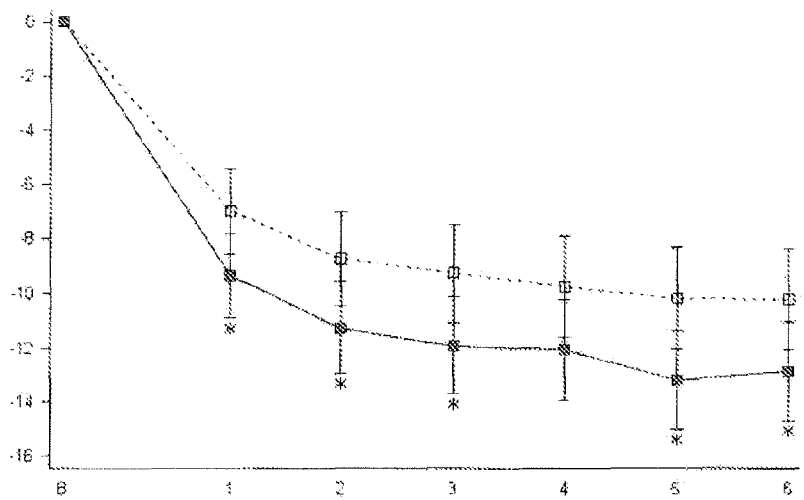

FIG. 8a: Study 12023A, high DRL at baseline and randomization, change in monthly HDD.

Figure 8B:
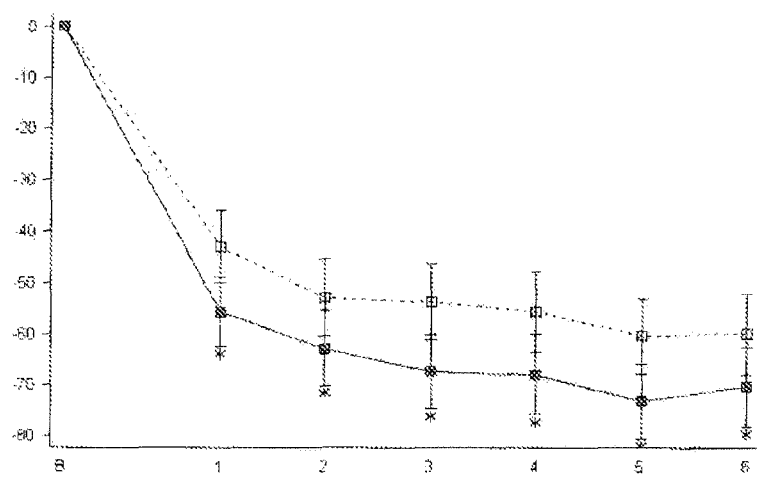

FIG. 8b: Study 12023A, high DRL at baseline and randomization, change in monthly TAC.

Figure 9A:
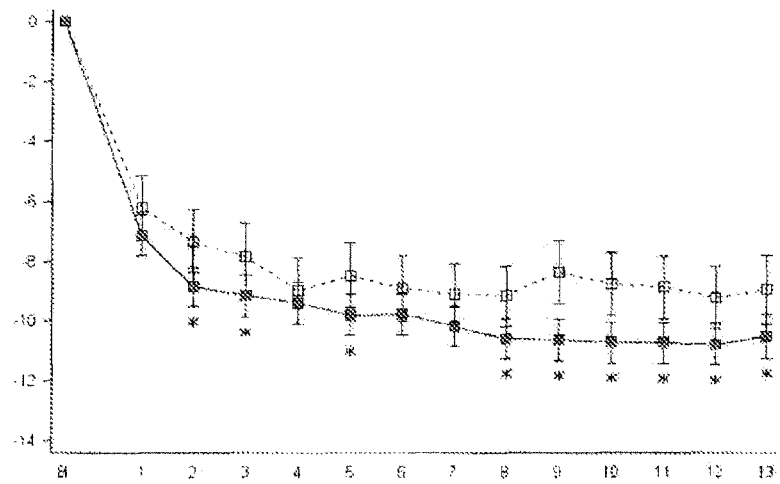

FIG. 9a: Study 12013A, total study population, change in monthly HDD.

Figure 9B:
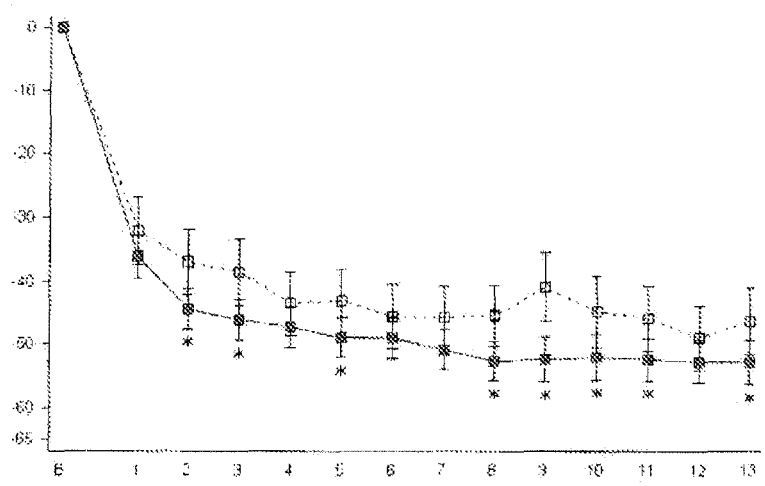

FIG. 9b: Study 12013A, total study population, change in monthly TAC.

Figure 10A:
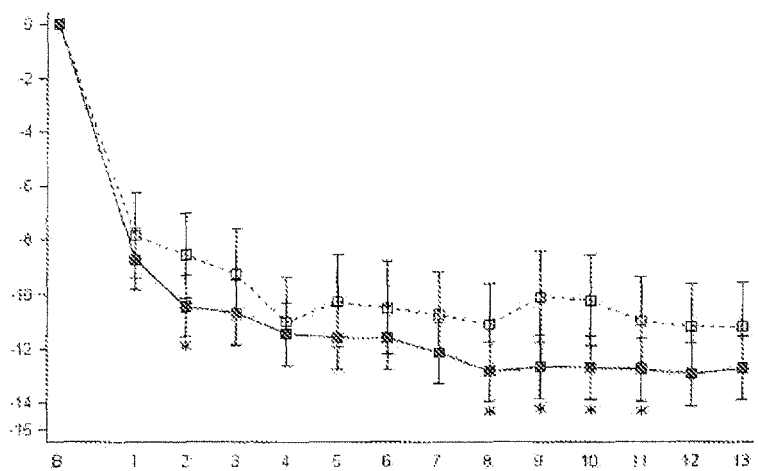

FIG. 10a: Study 12013A, high DRL at baseline, change in monthly HDD.

Figure 10B:
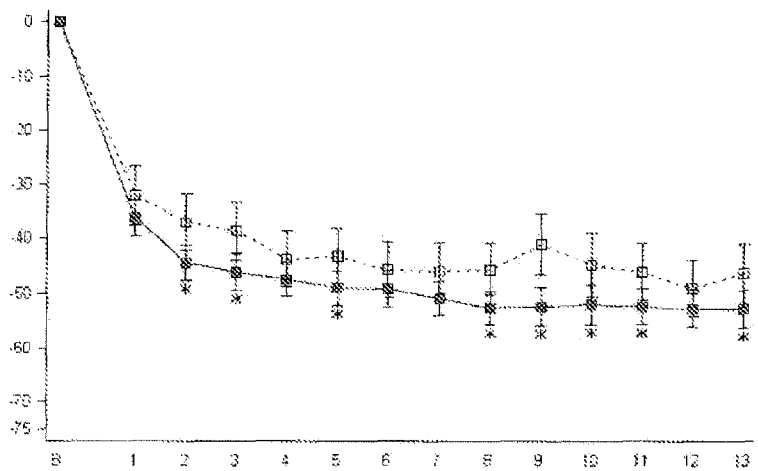

FIG. 10b: Study 12013A, high DRL at baseline, change in monthly TAC.

Figure 11A:
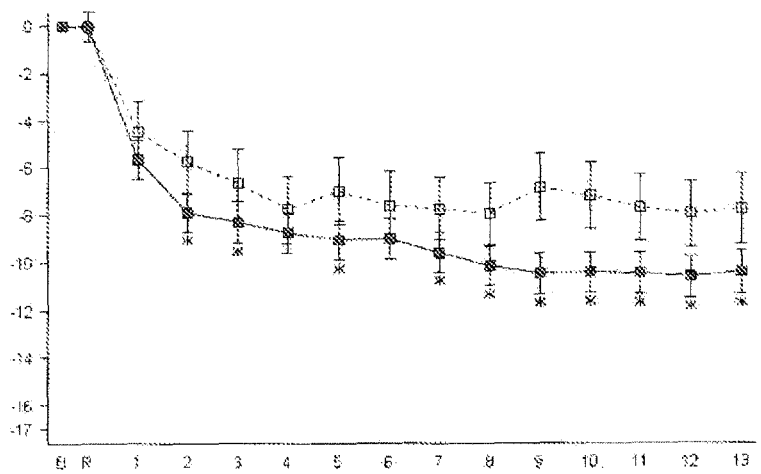

FIG. 11a: Study 12013A, total study population excluding ERs, change in monthly HDD.

Figure 11B:
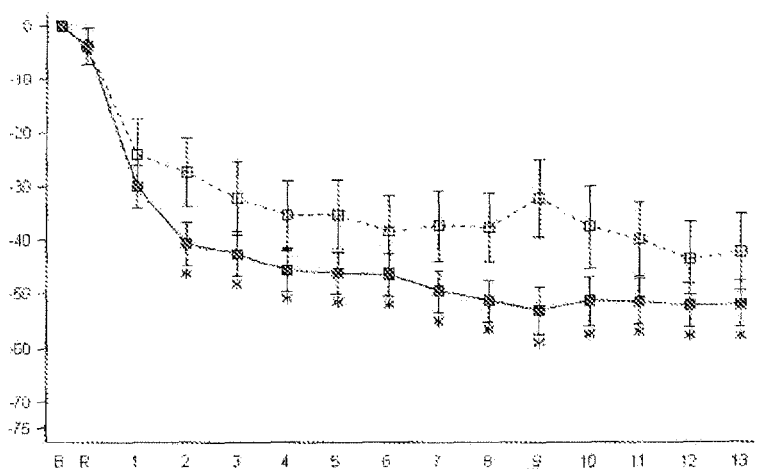

FIG. 11b: Study 12013A, total study population excluding ERs, change in monthly TAC.

Figure 12A:
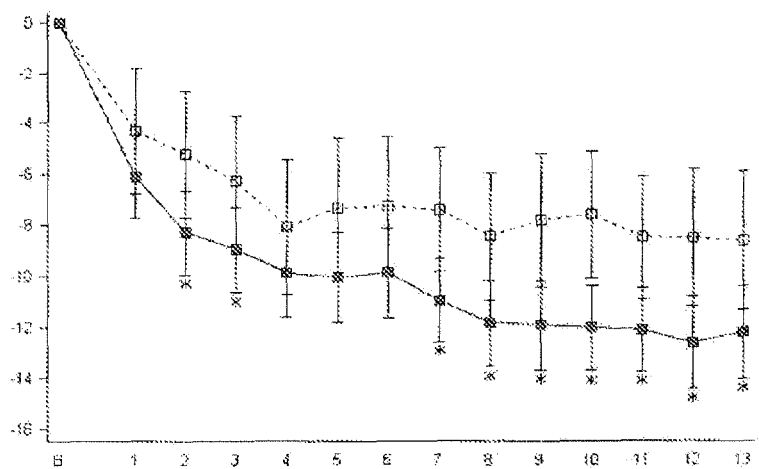

FIG. 12a: Study 12013A, high DRL at baseline and randomization, change in monthly HDD.

Figure 12B:
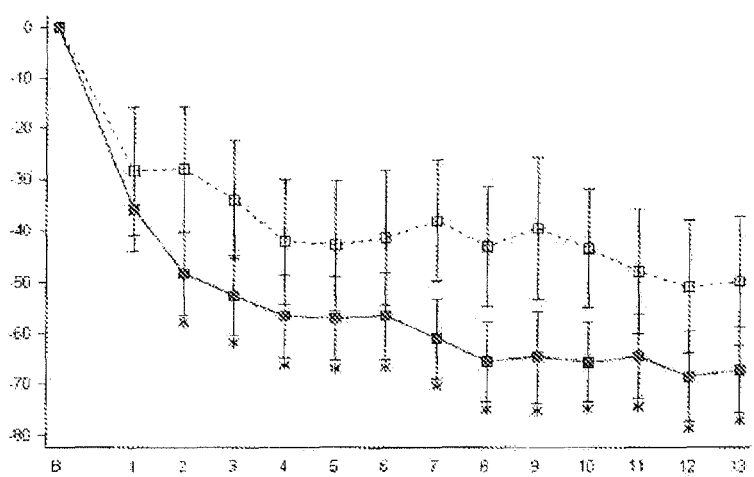

FIG. 12b: Study 12013A, high DRL at baseline and randomization, change in monthly TAC.

DEFINITIONS

Throughout the description, the term "nalmefene" is intended to include any forms of the compound, such as the free base and pharmaceutically acceptable salts. The free base and pharmaceutically acceptable salts include anhydrous forms and solvated forms such as hydrates. The anhydrous forms and the solvates include amorphous and crystalline forms. In a particular embodiment, nalmefene is in the form of the hydrochloride. In a more particular embodiment, nalmefene is in the form of the hydrochloride dihydrate. Throughout the application, when a dose is specified for nalmefene, said dose is calculated as the free base, i.e. when the nalmefene dose is 18 mg this corresponds to 18 mg of nalmefene free base.

As used herein, the term "total alcohol consumption" abbreviated TAG indicates mean daily total alcohol consumption measured in g/day over a month (=28 days).

As used herein, the term "heavy drinking day" abbreviated HDD indicates a day with a total alcohol consumption ≥60 g of pure alcohol for men and ≥40 g for women.

As used herein, "as-needed dosing" indicates that on each day a patient perceives a risk of drinking alcohol, one dose of nalmefene should be taken, preferably 1-2 hours prior to the anticipated time of drinking. If the patient has started drinking alcohol without taking nalmefene, the patient should take one dose as soon as possible after that.

As used herein, the term "drinking risk level" abbreviated DRL is defined according to WHOs criteria according to Table 1 below.

TABLE 1

WHO Drinking Risk Levels (DRLs) of Alcohol Consumption

| DRL | Total Alcohol Consumption (g/day) | |
|---|---|---|
| | Men | Women |
| Very high risk | >100 | >60 |
| High risk | >60 to 100 | >40 to 60 |
| Medium risk | >40 to 60 | >20 to 40 |
| Low risk | 1 to 40 | 1 to 20 |

Drinking Risk Levels according to Table 1 can be assessed e.g. by calculating mean daily alcohol consumption in g/day over a period such as 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year, Assessment of DRL can be performed by specialists and/or physicians such as general practitioners and/or other health care providers based on patients estimates of their alcohol consumption. In the three Lundbeck phase III studies described in the examples (12014A, 12023A and 12013A) DRL was measured by assessment of mean daily alcohol consumption in g/day over a 4 week period up to the initial visit. After a 1-2 week observation period the drinking risk level was re-assessed by assessment of mean daily alcohol consumption in g/day over said 1-2 week observation period.

Throughout the application, the term "high risk" or "at least high risk" is intended to include the two groups defined as "high risk" and "very high risk" ac cording to WHOs drinking risk levels listed in Table 1, i.e. patients having drinking risk level corresponding to a total alcohol consumption of >60 g/day of pure alcohol for men and >40 g/day for women. The present invention does not distinguish between patients with high and very high drinking risk levels, and when the terms "high drinking risk level" or "high DRL" are used in a claim or in an embodiment of the invention it is intended to include both the group defined as "high risk" and the group defined as "very high risk" according to WHOs drinking risk levels listed in Table 1.

As used herein, the term "early reducer" abbreviated ER indicates a patient included in the three Lundbeck phase III studies (12014A, 12023A and 12013A) who had considerably reduced the alcohol consumption in the period between screening and randomisation. More specifically, patients defined as ERs have reduced their alcohol consumption from high or medium DRL to a level below medium drinking risk level i.e. said patients had an alcohol consumption of 0-40 g/day for men and 0-20 g/day for women estimated as the mean daily alcohol consumption in a 1-2 week period between screening and randomization.

As used herein, an "observation period in accordance with clinical practice" is an observation following initial assessment of the DRL. Said period is preferably 1-2 weeks most preferably about 2 weeks.

As used herein, the term "adult" indicates a person who is at least 16 years old such as at least 18 years old.

As used herein, the term "adolescent" indicates a person who is 12-18 years old such as 12-16 years old.

As used herein, the terms "motivational support" and "counseling focused on enhanced treatment adherence and reduced alcohol consumption" indicate psychological motivation-enhancing interventions and can be used interchangeably with the terms "psychosocial support" or "psychosocial intervention focused on treatment adherence and reducing alcohol consumption". Said motivational support can be administered by a specialist and/or a physician such as a general practitioner and/or other health care providers. One example of such interventions is the BRENDA model, which is a time-limited, patient-centered clinical motivational intervention that complements the use of medication with focus on changing behavior and increasing medication adherence. The BRENDA model has been described by Starosta et al., *J. Psychiatr. Pract.* (2006), Vol. 12(2): 80-89, the entire contents of which are incorporated herein by reference. The term "initial motivational support" indicates such motivation-enhancing interventions provided to the patient prior to treatment with nalmefene. The term "ongoing motivational support" indicates such motivation-enhancing interventions provided to the patient concurrent to treatment with nalmefene e.g. on a recurrent basis.

As used herein, "Pharmaceutical composition" refers to a dose such as an oral dose form, such as a solid oral dose form, typically tablets or capsules. In a preferred embodiment, said dose form is suitable for as-needed dosing. Said pharmaceutical composition typically comprises a therapeutically effective amount of nalmefene and one or more pharmaceutically acceptable carrier. "Pharmaceutical compositions of the present invention" refers to all pharmaceutical compositions covered by the claims and description.

As used herein, a "unit dosage form" refers to a formulation unit of a pharmaceutical composition e.g. one tablet or capsule.

As used herein, "therapeutically effective amount" of a compound means the amount/dose of a compound or pharmaceutical composition that is sufficient to produce an effective response (i.e., a biological or medical response of a tissue, system, animal or human sought by a researcher, veterinarian, medical doctor or other clinician) upon administration to a patient. The "therapeutically effective amount" will vary depending on, inter alia, the disease and its severity, and on the age, weight, physical condition and responsiveness of the patient to be treated. Furthermore, the "therapeutically effective amount" may vary if the compound of the invention is combined with one or more compounds: In such a case the amount of a given compound might be lower, such as a sub-effective amount. In one embodiment, a "therapeutically effective amount" of nalmefene is 18 mg.

As used herein, "treatment" and "treating" refers to the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relieve the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications.

The term "alcohol dependence" is a commonly known term for a skilled person and is defined in the revised $4^{th}$ edition of the Diagnostic and Statistical Manual of Mental Disorders (DSM-IV-TR) (*Diagnostic and Statistical Manual of Mental Disorders,* $4^{th}$ edition text revision, American Psychiatric Publishing, 2000), the entire contents of which are incorporated herein by reference. As used herein, the term "alcohol dependence" is defined as the presence of three or more of the seven areas of life impairment related to alcohol in the same 12-month period. These impairments include 1) tolerance, 2) withdrawal, 3) the alcohol is often taken in larger amounts or over a longer period than was intended, 4) persistent desire or unsuccessful efforts to cut down or control alcohol intake, 5) a great deal of time is spent in activities necessary to obtain alcohol, intake alcohol, or recover from its effects, 6) important social, occupational, or recreational activities are given up or reduced because of alcohol consumption, 7) alcohol use is continued despite knowledge of having a persistent or recurrent physical or psychological problem that is likely to have been caused or exacerbated by alcohol consumption.

The term "alcohol use disorder" is defined in the $5^{th}$ edition of the Diagnostic and Statistical Manual of Mental Disorders (DSM-V) (Diagnostic and Statistical Manual of Mental Disorders, $5^{th}$ edition, American Psychiatric Publishing, 2013), the entire contents of which are incorporated herein by reference. As used herein, the term "alcohol use disorder" is defined as a problematic pattern of alcohol use leading to clinically significant impairment or distress, as manifested by at least two of the following, occurring within a 12-month period: 1) Alcohol is often taken in larger amounts or over a longer period than was intended. 2) There is a persistent desire or unsuccessful efforts to cut down or control alcohol use. 3) A great deal of time is spent in activities necessary to obtain alcohol, use alcohol, or recover from its effects. 4) Craving, or a strong desire or urge to use alcohol. 5) Recurrent alcohol use resulting in a failure to fulfill major role obligations at work, school, or home. 6) Continued alcohol use despite having persistent or recurrent social or interpersonal problems caused or exacerbated by the effects of alcohol. 7) Important social, occupational, or recreational activities are given up or reduced because of alcohol use. 8) Recurrent alcohol use in situations in which it is physically hazardous. 9) Alcohol use is continued despite knowledge of having a persistent or recurrent physical or psychological problem that is likely to have been caused or exacerbated by alcohol. 10) Tolerance, as defined by either of the following: a) A need for markedly increased amounts of alcohol to achieve intoxication or desired effect, b) A markedly diminished effect with continued use of the same amount of alcohol. 11) Withdrawal, as manifested by either of the following: a) The characteristic withdrawal syndrome for alcohol (refer to Criteria A and B of the criteria set for alcohol withdrawal). b) Alcohol (or a closely related substance, such as a benzodiazepine) is taken to relieve or avoid withdrawal symptoms. "Alcohol use disorder" is separated into the following three categories; Mild: Presence of 2-3 symptoms, Moderate: Presence of 4-5 symptoms, Severe: Presence of 6 or more symptoms.

The term "Timeline Follow-back" (TLFB) is a method to obtain estimates of daily drinking. Using memory aids, such as a calendar, patients provide retrospective estimates of the number of standard drinks for each day. In the three Lundbeck phase ill studies (12014A, 12023A and 12013A) TLFB was characterized by the following approach. A day was defined as a 24-hour period starting at 6.00 a.m. and ending at 6.00 a.m. the following morning. At the Screening Visit, each patient was to provide a retrospective estimate of his/her daily drinking over the previous month (a month was defined as a period of 28 consecutive days). At each subsequent visit, the patient was to provide information on his/her drinking since the previous visit. If a patient missed a visit, the TLFB that was completed at the next visit was extended to cover the days that should have been recorded at the missing visit. Patients could use their personal calendars to help them recalling their drinking or they could use a calendar provided by the site for their personal use. Calendars were only to be used as a memory aid to support the patients' input to TLFB. The patients were asked to report their alcohol intake by standard units according to the national definition of a standard unit. The standard national units were defined in standard drink conversion cards distributed to the patients.

"Hepatic impairment" can be assessed by the Child-Pugh scoring system, as defined in Child and Turcotte J G. *Surgery and portal hypertension. In: The liver and portal hypertension.* Edited by C G Child. Philadelphia: Saunders 1964:50-64, the entire contents of which are incorporated herein by reference. Patients can be classified according to this system with e.g. "moderate or severe hepatic impairment".

"Renal impairment" can be assessed by measuring estimated global filtration rate (eGFR) as described in Stevens et al., *N. Engl. J. Med.* (2006) 354:2473-2483, the entire contents of which are incorporated herein by reference. Patients with "severe renal impairment" are classified by an eGFR<30 ml/min per, 1.73 m$^2$.

DETAILED DESCRIPTION OF THE INVENTION

The efficacy of nalmefene in the reduction of alcohol consumption in patients with alcohol dependence (DSM-IV) has been evaluated in two efficacy studies (Study 12014A and Study 12023A) and one safety study (Study 12013A) as described in the examples. All three studies were randomized, double blind, parallel-group and placebo-controlled.

The studies included outpatients, aged ≥18 years, with a primary diagnosis of alcohol dependence. A patient was eligible for participation in the study if, in the 4 weeks preceding the Screening Visit (Baseline period), he/she had >6 HDDs, at least a medium DRL (calculated as mean daily alcohol consumption in g/day i.e. >40 g/day for men and >20 g/day for women calculated as mean daily alcohol consumption over the 4 week period preceding the screening visit), and ≤14 consecutive abstinent days. The timeline followback (TLFB) method was used to obtain estimates of the patient's daily drinking.

At the initial visit (screening visit), the patients' clinical status, social situation, and alcohol consumption pattern were evaluated. After a 1- to 2-week observation period the drinking risk level was re-assessed by calculating mean daily alcohol consumption in g/day over the 1- to 2-week observation period, and treatment with nalmefene was initiated together with counseling with focus on motivating the patients to adhere to the treatment and to change their drinking behavior.

The efficacy of nalmefene was measured using two co-primary endpoints: the change in the monthly number of heavy drinking days (HDDs) and the change in the mean daily total alcohol consumption (TAG) per month (=28 days). In the two 6 month efficacy studies and in the 12 month safety study, nalmefene was superior to placebo in reducing the number of HDDs and TAG at month 6 (see Table 6 and FIGS. 1, 5 and 9).

The inventors have found that in patients with a high DRL at baseline, i.e. alcohol consumption >60 g/day in men and >40 g/day in women at baseline (based on mean daily alcohol consumption in g/day over a 4 week period preceding the initial visit), the effect of nalmefene on HDDs and TAG was more pronounced compared to placebo than in the total population i.e. nalmefene has a better effect in this patient group than in the total study population (see Table 6 and FIGS. 2, 6 and 10). Therefore in one aspect, the present invention relates to nalmefene for use in the reduction of alcohol consumption in a patient with alcohol dependence who has a high drinking risk level i.e. a drinking risk level corresponding to >60 g/day of pure alcohol for men and >40 g/day for women. In one embodiment, the present invention relates to nalmefene for use in the reduction of alcohol consumption in a patient with alcohol dependence who has at a least high drinking risk level according to WHO criteria, such as a high or very high drinking risk level according to WHO criteria.

Furthermore, the inventors have observed that a sizeable proportion of the patients included in the three phase III studies (18%, 33% and 39% in studies 12014A, 12023A and 12013A, respectively) had considerably reduced their alcohol consumption in the 1- to 2-week observation period between screening and randomisation i.e. these patients had reduced their alcohol consumption from high Or medium DRL to below medium DRL in the 1- to 2-week observation period between screening and randomisation. These patients were characterized as Early Reducers (ERs). It was found that in the group of patients that were not ERs, the effect of nalmefene on HDDs and TAG was more pronounced compared to placebo than in the total population i.e. nalmefene has a better effect in this group of patients than in the total study population (see Table 6 and FIGS. 3, 7 and 11). Accordingly in another aspect the present invention relates to nalmefene for use in the reduction of alcohol consumption in a patient with alcohol dependence who maintains the level of alcohol consumption after an observation period in accordance with clinical practice, such as an observation period of 1-2 weeks. In one embodiment, the invention relates to nalmefene for use in the reduction of alcohol consumption in a patient with alcohol dependence who maintains at least medium DRL after an observation period in accordance with clinical practice, such as an observation period of 1-2 weeks.

It was found that in patients with a high DRL both at baseline and at randomisation; i.e. patients who had a high DRL at baseline based on mean daily alcohol consumption in g/day over a 4 week period preceding the initial visit and who maintained a high DRL in the 1- to 2-week observation period between screening and randomization; the effect of nalmefene on HDDs and TAC was even further pronounced compared to placebo than in the total population i.e. nalmefene has a particularly good effect in this group of patients compared to its effect in the total study population (see Table 6 and FIGS. 4, 8 and 12). Accordingly, in one embodiment the present invention relates to nalmefene for use in the reduction of alcohol consumption in a patient with alcohol dependence who have a high drinking risk level, i.e. alcohol consumption >60 g/day of pure alcohol for men and >40 g/day for women, and who continue to have a high drinking risk level after an observation period in accordance with clinical practice.

In one embodiment, patients according to the invention have a diagnosis of alcohol dependence according to the DSM-IV-TR criteria. In one embodiment, patients according to the invention have a diagnosis of alcohol use disorder according to the DSM-V criteria. In a further embodiment, patients according to the invention have a diagnosis selected from one or more of mild, moderate and severe alcohol use disorder according to the DSM-V criteria. In one embodiment, said patients have mild alcohol use disorder. In one embodiment, said patients have moderate alcohol use disorder. In one embodiment, said patients have severe alcohol use disorder.

In a separate aspect, the present invention relates to a method for conducting a clinical study for assessment of the efficacy of a treatment on the reduction of alcohol consumption, wherein the method comprises the following steps;
a) screening patients based on their drinking risk level,
b) re-assessing the drinking risk level after an observation period such as a 1- to 2-week observation period, such as a 2-week observation period,
c) excluding patients from the study who have considerably reduced their alcohol consumption in the observation period of step b).

In a further embodiment said patients selected for screening according to step a) have a primary diagnosis of DSM-IV alcohol dependence or DSM-V alcohol use disorder. In another further embodiment, said patients excluded in step c) have reduced their alcohol consumption to a drinking risk level from high or medium DRL to below medium DRL or from high DRL to below high DRL.

According to the present invention, nalmefene or a pharmaceutically acceptable alt thereof may be administered in any suitable way, e.g. orally or parenterally, and it may be presented in any suitable form for such administration, e.g. in the form of tablets, capsules, powders, syrups or solutions or dispersions for injection. In another embodiment, and in accordance with the purpose of the present invention, nalmefene is administered in the form of a solid pharmaceutical entity, suitably as a tablet or a capsule or in the form of a suspension, solution or dispersion for injection. Additionally, nalmefene may be administered with a pharmaceutically acceptable carrier, such as an adjuvant and/or diluent.

Methods for the preparation of solid or liquid pharmaceutical preparations are well known in the art. See e.g. Remington: The Science and Practice of Pharmacy, $21^{st}$ ed., Lippincott Williams & Wilkins (2005). Tablets may thus be prepared by mixing the active ingredients with an ordinary carrier, such as an adjuvant and/or diluent, and subsequently compressing the mixture in a tabletting machine. Non-limiting examples of adjuvants and/or diluents include: corn starch, lactose, talcum, magnesium stearate, gelatine, lactose, gums, and the like. Any other adjuvant or additive such as colorings, aroma, and preservatives may also be used provided that they are compatible with the active ingredients. The pharmaceutical compositions of the invention thus typically comprise a therapeutically effective amount of nalmefene and one or more pharmaceutically acceptable carrier. A suitable oral formulation of nalmefene is described in WO 2012/059103.

Without limiting the invention in any way, it is intended that any one of the aspects or embodiments of this patent application is suitable for the medicaments or pharmaceutical compositions described herein.

Nalmefene may be administered as an oral dose form, such as a solid oral dose form, typically tablets or capsules, or as a liquid oral dose form. Nalmefene may be administered in an immediate release dosage form or a controlled or sustained release dosage form. Nalmefene may be conveniently administered orally in unit dosage forms, such as tablets or capsules, containing the active ingredient in an amount from about 1 to about 100 mg, such as from 5 to 50 mg. Typically, the pharmaceutical composition comprises from 10 mg to 20 mg, such as about 10 mg, about 11 mg, about 12 mg, about 13 mg, about 14 mg, about 15 Mg, about 16 mg, about 17 mg, about 18 mg, about 19 mg or about 20 mg of nalmefene. In a preferred embodiment, the pharmaceutical composition comprises about 18 mg of nalmefene. In one embodiment, the unit dosage form comprises nalmefene in a therapeutically effective amount.

In one embodiment, nalmefene is taken as-needed, that is, on each day a patient perceives a risk of drinking alcohol, one dose of nalmefene should be taken, preferably 1-2 hours prior to anticipated time of drinking. In one embodiment, if the patient has started drinking alcohol without taking nalmefene, the patient should take one dose of nalmefene as soon as possible after that.

In one embodiment, nalmefene is in the form of the hydrochloride dihydrate.

Nalmefene according to the present invention is intended to be used for dosing in humans which are adults or adolescents. In one embodiment, nalmefene is intended to be used for dosing in humans 12 years or older, such as 14 years or older, such as 16 years or older, such as 18 years or older.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by con text).

It should be understood that the various aspects, embodiments, implementations and features of the invention mentioned herein may be claimed separately, or in any combination.

EMBODIMENTS ACCORDING TO THE INVENTION

In the following, embodiments of the invention are disclosed. The first embodiment is denoted E1, the second embodiment is denoted E2 and so forth.
E1. Nalmefene for use in the reduction of alcohol consumption in a patient with alcohol dependence who has a high DRL.

E2. Nalmefene according to embodiment 1, wherein said patient has a DRL corresponding to consumption >60 g/day of pure alcohol for men and >40 g/day for women.

E3. Nalmefene according to any of embodiments 1-2, wherein said DRL is assessed by calculating mean daily alcohol consumption in g/day over a period preceding assessment, wherein said period is 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer such as about 1 year.

E4. Nalmefene according to any of embodiments 1-3, wherein said patient has been identified as having a high DRL.

E5. Nalmefene according to any of embodiments 1-4, wherein said patient continues to have a high DRL despite initial motivational support.

E6. Nalmefene according to any of embodiments 1-4, wherein said patient maintains a high DRL after an observation period in accordance with clinical practice such as an observation period of 1-2 weeks, such as an observation period of about 2 weeks, E7. Nalmefene according to any of embodiments 1-5, wherein said patient maintains a high DRL after an observation period of 1-2 weeks following initial assessment of the DRL such as after an observation period of about 2 weeks following initial assessment of the DRL.

E8. Nalmefene according to any of embodiments 5-7, wherein said maintained high DRL is assessed by calculating mean daily alcohol consumption in g/day over said observation period.

E9. Nalmefene according to any of embodiments 5-8, wherein said maintained DRL corresponds to consumption >60 g/day of pure alcohol for men and >40 g/day for women.

E10. Nalmefene for use in the reduction of alcohol consumption in a patient with alcohol dependence who maintains the level of alcohol consumption despite initial motivational support.

E11. Nalmefene for use in the reduction of alcohol consumption in a patient who maintains the level of alcohol consumption after an observation period in accordance with clinical practice such as an observation period of 1-2 weeks, such as an observation period of about 2 weeks.

E12. Nalmefene for use in the reduction of alcohol consumption in a patient with alcohol dependence who maintains at least medium DRL after an observation period following initial assessment such as an observation period of 1-2 weeks, such as an observation period of about 2 weeks.

E13. Nalmefene according to embodiments 10-12, wherein said maintained DRL corresponds to consumption >40 g/day of pure alcohol for men and >20 g/day for women.

E14. Nalmefene according to any of embodiments 10-13, wherein said patient has a high DRL at initial assessment.

E15. Nalmefene according to embodiment 14, wherein said patient has a DRL corresponding to consumption >60 g/day of pure alcohol for men and >40 g/day for women at initial assessment.

E16. Nalmefene according to any of embodiments 14-15, wherein said patient maintains a high DRL after said observation period.

E17. Nalmefene according to any of embodiments 10-16, wherein said maintained DRL is assessed by calculating mean daily alcohol consumption in g/day over said observation period.

E18. Nalmefene according to any of embodiments 14-17, wherein said high DRL at initial assessment is assessed by calculating mean daily alcohol consumption in g/day over a period preceding assessment, wherein said period is 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year.

E19. Nalmefene according to any of embodiments 14-18, wherein said patient has been identified as having a high DRL.

E20. Nalmefene for use in reduction of alcohol consumption in a patient with alcohol dependence who has a DRL corresponding to consumption >60 g/day of pure alcohol for men and >40 g/day for women assessed by calculating mean daily alcohol consumption in g/day over a period preceding assessment; wherein said patient maintains a DRL corresponding to consumption >60 g/day of pure alcohol for men and >40 g/day for women after an observation period following initial assessment, assessed by calculating mean daily alcohol consumption in g/day over said observation period.

E21. Nalmefene according to embodiment 20, wherein said period preceding assessment is 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year.

E22. Nalmefene according to any of embodiments 20-21, wherein said observation period following initial assessment is 1-2 weeks such as about 2 weeks.

E23. Nalmefene according to any of embodiments 1-22, wherein said nalmefene is to be used as-needed, such as on each day the patient perceives a risk of drinking alcohol, preferably 1-2 hours prior to the anticipated time of drinking.

E24. Nalmefene for use in reduction of alcohol consumption in a patient with alcohol dependence, wherein said use comprises the following steps;
a) identifying a patient with alcohol dependence i) who has a high DRL, and/or iii who maintains the DRL of alcohol consumption after an observation period following initial assessment, and
b) administering nalmefene to the patient identified in step a), wherein said nalmefene is to be administered as-needed, such as on each day the patient perceives a risk of drinking alcohol, preferably 1-2 hours prior to the anticipated time of drinking.

E25. Nalmefene according to embodiment 24, wherein said observation period following initial assessment is 1-2 weeks, such as about 2 weeks.

E26. Nalmefene according to any of embodiments 21-25, wherein said patient identified in step a) has a DRL corresponding to consumption >60 g/day of pure alcohol for men and >40 g/day for women.

E27. Nalmefene according to any of embodiments 24-26, wherein said high DRL identified in step a) i) has been assessed by calculating mean daily alcohol consumption in g/day over a period preceding assessment, wherein said period os 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year.

E28 Nalmefene according to any of embodiments 24-27, wherein said maintained DRL in step a) ii) is assessed by calculating mean daily alcohol consumption in g/day over said observation period.

E29. Nalmefene according to any of embodiments 1-28, wherein said patient does not require immediate detoxification and/or wherein said patient does not have physical withdrawal symptoms.

E30. Nalmefene according to any of embodiments 1-29, wherein said patient is subject to ongoing motivational support.

E31. Nalmefene according to any of embodiments 1-30, wherein said patient is subject to counseling focused on enhanced treatment adherence and reduced alcohol consumption.

E32. Nalmefene according to embodiment 31, wherein said counseling is performed according to the BRENDA model, E33. Nalmefene according to any of embodiments 1-32, wherein said patient is a patient for whom immediate abstinence is not a treatment goal.

E34. Nalmefene according to any of embodiments 1-33, wherein said nalmefene is to be used for a treatment period of 6-12 months, such as 6 months.

E35. Nalmefene according to any of embodiments 1-34, wherein said patient is an adult or an adolescent.

E36. Nalmefene according to any of embodiments 1-35, wherein said patient is 12 years or older, such as 14 years or older, such as 16 years or older, such as 18 years or older.

E37. Nalmefene according to any of embodiments 1-36, wherein said nalmefene is used in a dose of 10-20 mg such as 10 mg, 11 mg, 12 mg, 13 mg, 14 mg, 15 mg, 16 mg, 17 mg, 18 mg, 19 mg or 20 mg.

E38. Nalmefene according to embodiment 37, wherein said nalmefene is used in a dose of 18 mg.

E39. Nalmefene according to any of embodiments 1-38, wherein said nalmefene is used in the form of a pharmaceutically acceptable acid addition salt.

E40. Nalmefene according to embodiment 39, wherein said nalmefene is used in the form of the hydrochloride salt.

E41. Nalmefene according to embodiment 40, wherein said nalmefene is used in the form of the hydrochloride dihydrate.

E42. Nalmefene according to any of embodiments 1-41, wherein said nalmefene is used in a crystalline form.

E43. Nalmefene according to any of embodiments 1-42, wherein said nalmefene is used in an oral dose form such as tablets or capsules.

E44. Nalmefene according to any of embodiments 1-43, wherein said nalmefene is used in combination with a further active ingredient.

E45. Nalmefene according to any of embodiments 1-44, wherein said patient does not fall into one or more of the following categories: patients taking opioid analgesics, opioid-addicted patients without successful withdrawal, patients with acute symptoms of opioid withdrawal, patients for whom re cent use of opioids is suspected, patients with moderate or severe hepatic impairment, patients with moderate or severe renal impairment, patients with current or recent opioid addiction, patients with a recent history of acute alcohol withdrawal syndrome (including hallucinations, seizures, and delirium tremens).

E46. A method for reduction of alcohol consumption in a patient with alcohol dependence who has a high DRL, which method comprises the administration of a therapeutically effective amount of nalmefene to said patient.

E47. The method according to embodiment 46, wherein said patient has a DRL corresponding to consumption >50 g/day of pure alcohol for men and >40 g/day for women.

E48. The method according to any of embodiments 46-47, wherein said DRL is assessed by calculating mean daily alcohol consumption in g/day over a period preceding assessment, wherein said period is 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year.

E49. The method according to any of embodiments 46-48, wherein said patient has been identified as having a high DRL.

E50. The method according to any of embodiments 46-49, wherein said patient continues to have a high DRL despite initial motivational support.

E51. The method according to any of embodiments 46-50, wherein said patient maintains a high DRL after an observation period in accordance with clinical practice such as an observation period of 1-2 weeks such as an observation period of about 2 weeks.

E52 The method according to any of embodiments 46-50, wherein said patient maintains a high DRL after an observation period of least 1 week following initial assessment of the DRL such as after an observation period of about 2 weeks following initial assessment of the DRL.

E53. The method according to any of embodiments 50-52, wherein said maintained high DRL is assessed by calculating mean daily alcohol consumption in g/day over said observation period.

E54. The method according to any of embodiments 50-53, wherein said maintained DRL corresponds to consumption >60 g/day of pure alcohol for men and >40 g/day for women.

E55. A method for reduction of alcohol consumption in a patient with alcohol dependence who maintains the level of alcohol consumption despite initial motivational support, which method comprises the administration of a therapeutically effective amount of nalmefene to said patient.

E56. A method for reduction of alcohol consumption in a patient with alcohol dependence who maintains the level of alcohol consumption after an observation period in accordance with clinical practice such as an observation period of 1-2 weeks such as an observation period of about 2 weeks, which method comprises the administration of a therapeutically effective amount of nalmefene to said patient.

E57. A method for reduction of alcohol consumption in a patient with alcohol dependence who maintains at least medium DRL after an observation period following initial assessment such as an observation period of 1-2 weeks, such as an observation period of about 2 weeks, which method comprises the administration of a therapeutically effective amount of nalmefene to said patient.

E58. The method according to embodiments 55-57, wherein said maintained DRL corresponds to consumption >40 g/day of pure alcohol for men and >20 g/day for women.

E59. The method to any of embodiments 55-58, wherein said patient has a high DRL at initial assessment, E60. The method according to embodiment 59, wherein said patient has a DRL corresponding to consumption >60 g/day of pure alcohol for men and >40 g/day for women at initial assessment.

E61. The method according to any of embodiments 55-60, wherein said patient maintains a high DRL after said observation period.

E62. The method according to any of embodiments 55-61, wherein said maintained DRL is assessed by calculating mean daily alcohol consumption in g/day over said observation period.

E63. The method according to any of embodiments 59-62, wherein said high DRL at initial assessment is assessed by calculating mean daily alcohol consumption in g/day over a period preceding assessment, wherein said period is 1 week or longer, such as 2 weeks or longer such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year.

E64. The method according to any of embodiments 59-63, where said patient has been identified as having a high DRL.

E65. A method for reduction of alcohol consumption in a patient with alcohol dependence who has a DRL corresponding to consumption >60 g/day of pure alcohol for men and >40 g/day for women assessed by calculating mean dairy alcohol consumption in g/day over a period preceding assessment, wherein said patient maintains a DRL corresponding to consumption >60 g/day of pure alcohol for men and >40 g/day for women after an observation following initial assessment, assessed by calculating mean daily alcohol consumption in g/day over said observation period, which method comprises the administration of a therapeutically effective amount of nalmefene to said patient.

E66. The method according to embodiment 65, wherein said period preceding assessment is 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year.

E67. The method according to any of embodiments 65-66, wherein said observation period in following initial assessment is 1-2 weeks such as about 2 weeks.

E68. The method according to any of embodiments 46-67, wherein said nalmefene is administered as-needed, such as on each day the patient perceives a risk of drinking alcohol, preferably 1-2 hours prior to the anticipated time of drinking.

E69. A method for reduction of alcohol consumption in a patient with alcohol dependence, wherein said method comprises the following steps;
 a) identifying a patient with alcohol dependence i) who has a high DRL, and/or ii) who maintains the DRL of alcohol consumption after an observation period following initial assessment, and
 b) administering a therapeutically effective amount of nalmefene to the patient identified in step a), wherein said nalmefene is to be administered as-needed; such as on each day the patient perceives a risk of drinking alcohol, preferably 1-2 hours prior to the anticipated time of drinking.

E70. The method according to embodiment 69, wherein said observation period following initial assessment is 1-2 weeks, such as about 2 weeks.

E71. The method according to any of embodiments 69-70, wherein the patient identified in step a) has a DRL corresponding to consumption >60 g/day of pure alcohol for men and >40 g/day for women.

E72. The method according to any of embodiments 69-71, wherein said high DRL identified in step a) i) has been assessed by calculating mean daily alcohol consumption in g/day over a period preceding assessment, wherein said period is 1 week or longer, such as 2 weeks or longer, such as 3 weeks or longer, such as 4 weeks or longer, such as 1 month or longer such as 2 months or longer; such as 3 months or longer, such as 4 months or longer, such as 5 months or longer, such as 6 months or longer, such as about 1 year.

E73. The method according to any of embodiments 69-72, wherein said maintained DRL in step a) ii) is assessed by calculating mean daily alcohol consumption in g/day over said observation period.

E74. The method according to any of embodiments 46-73, wherein said patient does not require immediate detoxification and/or wherein said patient does not have physical withdrawal symptoms.

E75. The method according to any of embodiments 46-74, wherein said patient is subject to ongoing motivational support.

E76. The method according to any of embodiments 46-76, wherein said patient is subject to counseling focused on enhanced treatment adherence and reduced alcohol consumption.

E77. The method according to embodiment 76, wherein said counseling is performed according to the BRENDA model.

E78. The method according to any of embodiments 46-77, wherein said patient is a patient for whom immediate abstinence is not a treatment goal.

E79. The method according to any of embodiments 46-78, wherein said nalmefene is to be used for a treatment period of 6-12 months, such as 6 months.

E80. The method according to any of embodiments 46-79, wherein said patient is an adult or an adolescent.

E81. The method according to any of embodiments 46-80, wherein said patient is 12 years or older, such as 14 years or older, such as 16 years or older, such as 18 years or older.

E82. The method according to any of embodiments 46-81, wherein the amount of nalmefene is 10-20 mg such as 10 mg, 11 mg, 12 mg, 13 mg, 14 mg, 15 mg, 16 mg, 17 mg, 18 mg, 19 mg or 20 mg.

E83. The method according to embodiment 82, wherein the amount of nalmefene is 18 mg.

E84. The method according to any of embodiments 46-83, wherein said nalmefene is administered in the form of a pharmaceutically acceptable acid addition salt.

E85. The method according to embodiment 84, wherein said nalmefene is administered in the form of the hydrochloride salt.

E86. The method according to embodiment 85, wherein said nalmefene is administered in the form of the hydrochloride dihydrate.

E87. The method according to any of embodiments 46-86, wherein said nalmefene is administered in a crystalline form.

E88. The method according to any of embodiments 46-87, wherein said nalmefene is administered in an oral dose form such as tablets or capsules.

E89. The method according to any of embodiments 46-88, wherein said nalmefene is administered in combination with a further active ingredient.

E90. The method according to any of embodiments 46-89, wherein said patient does not fall into one or more of the following categories: patients taking opioid analgesics, opioid-addicted patients without successful withdrawal, patients with acute symptoms of opioid withdrawal, patients for whom recent use of opioids is suspected, patients with moderate or severe hepatic impairment, patients with moderate or severe renal impairment, patients with current or recent opioid addiction, patients with a recent history of acute alcohol withdrawal syndrome (including hallucinations, seizures, and delirium tremens).

E91. Use of nalmefene for the manufacture of a medicament for reduction of alcohol consumption in a patient with alcohol dependence who has a high DRL.

E92. The use according to embodiment 91, wherein said patient has a DRL corresponding to consumption >60 g/day of pure alcohol for men and >40 g/day for women.

E93. The use according to any of embodiments 91-92, wherein said DRL is assessed by calculating mean daily alcohol consumption in g/day over a period preceding assessment, wherein said period is 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year E94. The use according to any of embodiments 91-93, wherein said patient has been identified as having a high DRL.

E95. The use according to any of embodiments 91-94, wherein said patient continues to have a high DRL despite initial motivational support.

E96. The use according to any of embodiments 91-95, wherein said patient maintains a high DRL after an observation period in accordance with clinical practice such as an observation period of 1-2 weeks such as an observation period of about 2 weeks.

E97. The use according to any of embodiments 91-95, wherein said patient maintains a high DRL after an observation period of 1-2 weeks following initial assessment of the DRL such as after an observation period of about 2 weeks following initial assessment of the DRL.

E98. The use according to any of embodiments 95-97, wherein said maintained high DRL is assessed by calculating mean daily alcohol consumption in g/day over said observation period.

E99. The use according to any of embodiments 95-98, wherein said maintained DRL corresponds to consumption >60 g/day of pure alcohol for men and >40 g/day for women.

E100. Use of nalmefene for the manufacture of a medicament for reduction of alcohol consumption in a patient with alcohol dependence who maintains the level of alcohol consumption despite initial motivational support.

E101. Use of nalmefene for the manufacture of a medicament for reduction of alcohol consumption in a patient who maintains the level of alcohol consumption after an observation period in accordance with clinical practice such as an observation period of 1-2 weeks, such as an observation period of about 2 weeks, E102. Use of nalmefene for the manufacture of a medicament for reduction of alcohol consumption in a patient with alcohol dependence who maintains at least medium DRL after an observation period following initial assessment such as an observation period of 1-2 weeks, such as an observation period of 2 weeks.

E103. The use according to any of embodiments 100-102, wherein said maintained DRL corresponds to consumption >40 g/day of pure alcohol for men and >20 g/day for women.

E104. The use according to any of embodiments 100-103, wherein said patient has a high DRL at initial assessment.

E105. The use according to embodiment 104, wherein said patient has a DRL, corresponding to consumption >60 g/day of pure alcohol for men and >4 g/day for women at initial assessment.

E106. He use according to any of embodiments 101-105, wherein said patient maintains a high DRL after said observation period.

E107. The use according to any of embodiments 101-106, wherein said maintained DRL is assessed by calculating mean daily alcohol consumption in g/day over said observation period.

E108. The use according to any of embodiments 104-107, wherein said high DRL at initial assessment is assessed by calculating mean daily alcohol consumption in g/day over a period preceding assessment, wherein said period is 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year.

E109. The use according to any of embodiments 104-108, wherein said patient has been identified as having a high DRL.

E110. Use of nalmefene for the manufacture of a medicament for reduction of alcohol consumption in a patient with alcohol dependence who has a DRL corresponding to consumption >60 g/day of pure alcohol for men and >40 g/day for women assessed by calculating mean daily alcohol consumption in g/day over a preceding assessment, wherein said patient maintains a DRL corresponding to consumption >60 g/day of pure alcohol for men and >40 g/day for women after an observation period following initial assessment, assessed by calculating mean daily alcohol consumption in g/day over said observation period.

E111. The use according to embodiment 110, wherein said period preceding assessment is 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year.

E112. The use according to any of embodiments 110-111, wherein said observation period following initial assessment is 1-2 weeks such as about 2 weeks.

E113 The use according to any of embodiments 91-112, wherein said medicament is to be taken as-needed, such as on each day the patient perceives a risk of drinking alcohol, preferably 1-2 hours prior to the anticipated time of drinking.

E114. Use of nalmefene for the manufacture of a medicament for reduction of alcohol consumption in a patient with alcohol dependence, wherein said use comprises the following steps;
a) manufacturing a medicament comprising nalmefene,
b) identifying a patient with alcohol dependence i) who has a high DRL, and/or ii) who maintains the DRL of alcohol consumption after an observation period following initial assessment, and c) administering said medicament to the patient identified in step b), wherein said medicament is to be administered as-needed, such as on each day the patient perceives a risk of drinking alcohol, preferably 1-2 hours prior to the anticipated time of drinking.

E115. The use according to embodiment 114, wherein said observation period following initial assessment is 1-2 weeks, such as 2 weeks.

E116. The use according to any of embodiments 114-115, wherein said patient identified in step b) has a DRL corresponding to consumption >60 g/day of pure alcohol for men and >40 g/day for women.

E117. The use according to any of embodiments 114-116, wherein said high DRL in identified in step b) i) has been assessed by calculating mean daily alcohol consumption in g/day over a period preceding assessment, wherein said period is 1 week or longer, such as 2 weeks or longer, such as 3 weeks or longer, such as 4 weeks or longer, such as 1 month or longer such as 2 months or longer, such as 3 months or longer, such as 4 months or longer, such as 5 months or longer, such as 6 months or longer, such as about 1 year.

E118. Nalmefene according to any of embodiments 114-117, wherein said maintained DRL in step b) ii) is assessed by calculating mean daily alcohol consumption in g/day over said observation period, E119. The use according to any of embodiments 91-118, wherein said patient does not require immediate detoxification and/or wherein said patient does not have physical withdrawal symptoms.

E120. The use according to any of embodiments 91-119, wherein said patient is subject to ongoing motivational support.

E121. The use according to any of embodiments 91-120, wherein said patient is subject to counseling focused on enhanced treatment adherence and reduced alcohol consumption.

E122. The use according to embodiment 121, wherein said counseling is performed according to the BRENDA model.

E123. The use according to any of embodiments 91-122, wherein said patient is a patient for whom immediate abstinence is not a treatment goal.

E124. The use according to any of embodiments 91-123, wherein said medicament is to be used for a treatment period of 6-12 months such as 6 months.

E125. The use according to any of embodiments 91-124, wherein said patient is an adult or an adolescent.

E126. The use according to any of embodiments 91-125, wherein said patient is 12 years or older, such as 14 years or older, such as 16 years or older, such as 18 years or older.

E127. The use according to any of embodiments 91-126, wherein said medicament comprises nalmefene in a dose of 10-20 mg such as 10 mg, 11 mg, 12 mg, 13 mg, 14 mg, 15 mg, 16 mg, 17 mg, 18 mg, 19 mg or 20 mg.

E128. The use according to embodiment 127, wherein said medicament comprises nalmefene in a dose of 18 mg.

E129. The use according to any of embodiments 91-128, wherein said medicament comprises nalmefene in the form of a pharmaceutically acceptable acid addition salt.

E130. The use according to embodiment 129, wherein said medicament comprises nalmefene in the form the hydrochloride salt.

E131. The use according to embodiment 130, wherein said medicament comprises nalmefene in the form the hydrochloride dihydrate.

E132. The use according to any of embodiments 91-131, wherein said said medicament comprises nalmefene in a crystalline form.

E133. The use according to any of embodiments 91-132, wherein said medicament comprises an oral dose form such as tablets or capsules.

E134. The use according to any of embodiments 91-133, wherein said medicament comprises a further active ingredient.

E135. The use according to any of embodiments 91-134, wherein said patient does not fall into one or more of the following categories: patients taking opioid analgesics, opioid-addicted patients without successful withdrawal, patients with acute symptoms of opioid withdrawal, patients for whom recent use of opioids is suspected, patients with moderate or severe hepatic impairment, patients with moderate or severe renal impairment, patients with current or recent opioid addiction, patients with a recent history of acute alcohol withdrawal syndrome (including hallucinations, seizures, and delirium tremens).

EXAMPLES

The invention will be illustrated by the following non-limiting examples.

The efficacy of nalmefene on the reduction of alcohol consumption in patients with alcohol dependence (DSM-IV) was evaluated in two efficacy studies (Study 12014A and Study 12023A). Both studies were randomised, double blind, two-parallel group, placebo controlled, and after 6 months of treatment, patients receiving nalmefene were re-randomised to receive either placebo or nalmefene in a 1 month run out period. The efficacy of nalmefene was also evaluated in a randomised, double blind, two parallel group, placebo controlled 1 year safety study (Study 12013A). The studies included 1941 patients, 1144 of whom were treated with nalmefene 18 mg in an as-needed dosing regimen.

The studies were conducted applying an outpatient setting without preceding detoxification. Higher CIWA withdrawal scores (Clinical Institute Withdrawal Assessment for Alcohol) at screening as well as a history of delirium tremens and seizures would be indicative for the necessity of prior inpatient detoxification. Patients with abuse of substance other than alcohol and subjects with significant depressive or psychotic co-morbidity were excluded.

The studies included outpatients, aged ≥18 years, with a primary diagnosis of alcohol dependence. A patient was eligible for participation in the study if in the 4 weeks preceding the Screening Visit (Baseline period), he/she had >6 HDDs, at least a medium DRL (calculated as mean daily alcohol consumption in g/day i.e. >40 g/day for men and >20 g/day for women calculated as mean daily alcohol consumption over the 4 week period preceding the screening visit), and ≤14 consecutive abstinent days. The timeline followback (TLFB) method was used to obtain estimates of the patient's daily drinking.

The studies were conducted over a 34 week period (12 visits) in total and consisted of four sequential periods: a 2-week screening period, a 24-week double-blind treatment period, a 4-week double-blind placebo-controlled run-out in each of the treatment arms and finally a 4-week safety follow-up. One to two weeks after the Screening Visit the patients were randomised 1:1 to 24 weeks of as-needed, double-blind treatment (Main Treatment Period; MTP) with nalmefene (18 mg) or placebo. The patients who completed 24 weeks of double-blind treatment entered a 4-week, double-blind Run-out Period (ROP). The patients randomised to nalmefene were re-randomised 1:1 to receive nalmefene (18 mg, as-needed) or placebo and the patients randomised to placebo continued on placebo.

The Timeline Follow-back (TLFB) method was used to collect self-reported drinking data (alcohol consumption).

At the initial visit, the patients' clinical status, social situation, and alcohol consumption pattern were evaluated (based on patient reporting). After a 1- to 2-week observation period the drinking risk level was re-assessed (i.e. the mean daily alcohol consumption over the 1-2 week assessment period was calculated), and treatment with nalmefene was initiated together with counseling with focus on motivating the patients to adhere to the treatment and to change their drinking behavior. In all the studies, a motivational and adherence enhancing intervention, according to the BRENDA model, was administered to all the patients to support the patients in changing their behavior and to enhance adherence to treatment.

The patients alcohol intake (g/day) was estimated based on national definitions of standard units (subsequently converted into grams of alcohol). To define the standard units, a standard drink conversion card was distributed to each patient at the Screening Visit. Each patient was also provided with a calendar that he/she could use to support his/her input to the TLFB, or he/she could use a personal calendar, if preferred. For all the variables derived from the TLFB data baseline was defined as the month (that is, 4 weeks/28 consecutive days) preceding the Screening Visit. The investigational medicinal product (IMP) was taken as-needed. Each patient was instructed to take a maximum of one tablet on each day the patient perceived a risk of drinking alcohol, preferably 1 to 2 hours prior to the anticipated time of drinking. If the patient had started drinking alcohol without taking nalmefene, the patient as to take one tablet as soon as possible. The dates when nalmefene was taken/not taken were recorded using the TLFB method. The chosen comparator was placebo The demographic data for each study are provided in tables 2-4 below. Table 5 summarizes the number of patients in the efficacy analysis for each patient group.

TABLE 2

Patient Demographics (APRS) - Study 12014A

| | | Placebo | Nalmefene | Total |
|---|---|---|---|---|
| Number of Patients | | 298 | 306 | 604 |
| Age (years) | N | 298 | 306 | 604 |
| | MEAN | 52.12 | 51.02 | 51.56 |
| | STD | 9.08 | 10.12 | 9.63 |
| | MIN | 24.00 | 24.00 | 24.00 |
| | MAX | 75.00 | 72.00 | 75.00 |
| | MEDIAN | 52.00 | 51.00 | 52.00 |
| Age group (years) n (%) | <25 | 1 (0.3) | 1 (0.3) | 2 (0.3) |
| | >=25 and <35 | 6 (2.0) | 14 (4.6) | 20 (3.3) |
| | >=35 and <45 | 54 (18.1) | 65 (21.2) | 119 (19.7) |
| | >=45 and <55 | 115 (38.6) | 108 (35.3) | 223 (36.9) |
| | >=55 and <65 | 97 (32.6) | 87 (28.4) | 184 (30.5) |
| | >=65 | 25 (8.4) | 31 (10.1) | 56 (9.3) |
| Sex n (%) | F | 96 (32.2) | 102 (33.3) | 198 (32.5) |
| | M | 202 (67.8) | 204 (66.7) | 406 (67.2) |

TABLE 2-continued

Patient Demographics (APRS) - Study 12014A

| | | Placebo | Nalmefene | Total |
|---|---|---|---|---|
| Race n (%) | BLACK | 1 (0.3) | | 1 (0.2) |
| | CAUCASIAN | 297 (99.7) | 306 (100) | 603 (99.5) |

TABLE 3

Patient Demographics (APRS) - Study 12023A

| | | Placebo | Nalmefene | Total |
|---|---|---|---|---|
| Number of Patients | | 360 | 358 | 718 |
| Age (years) | N | 360 | 358 | 718 |
| | MEAN | 44.41 | 45.10 | 44.75 |
| | STD | 10.66 | 10.69 | 10.67 |
| | MIN | 20.00 | 20.00 | 20.00 |
| | MAX | 69.00 | 72.00 | 72.00 |
| | MEDIAN | 45.00 | 45.00 | 45.00 |
| Age group (years) n (%) | <25 | 7 (1.9) | 9 (2.5) | 16 (2.2) |
| | >=25 and <35 | 69 (19.2) | 57 (15.9) | 126 (17.5) |
| | >=35 and <45 | 99 (27.5) | 106 (29.6) | 205 (28.6) |
| | >=45 and <55 | 123 (34.2) | 118 (32.4) | 239 (33.3) |
| | >=55 and <55 | 52 (14.4) | 57 (15.9) | 109 (15.2) |
| | >=65 | 10 (2.8) | 13 (3.6) | 23 (3.2) |
| Sex n (%) | F | 104 (28.9) | 92 (25.7) | 196 (27.3) |
| | M | 256 (71.1) | 266 (74.3) | 522 (72.7) |
| Race n (%) | ASIAN | | 2 (0.6) | 2 (0.3) |
| | BLACK | 2 (0.6) | 3 (0.8) | 5 (0.7) |
| | CAUCASIAN | 357 (99.2) | 353 (98.6) | 710 (98.9) |
| | OTHER | 1 (0.3) | | 1 (0.1) |

TABLE 4

Patient Demographics (APRS) - Study 12013A

| | | Placebo | Nalmefene | Total |
|---|---|---|---|---|
| Number of Patients | | 166 | 509 | 675 |
| Age (years) | N | 166 | 509 | 675 |
| | MEAN | 44.27 | 44.26 | 44.26 |
| | STD | 11.99 | 11.24 | 11.42 |
| | MIN | 18.00 | 19.00 | 18.00 |
| | MAX | 72.00 | 77.00 | 77.00 |
| | MEDIAN | 44.00 | 44.00 | 44.00 |
| Age group (years) n (%) | <25 | 8 (4.8) | 14 (2.8) | 22 (3.3) |
| | >=25 and <35 | 30 (18.1) | 91 (17.9) | 121 (17.9) |
| | >=35 and <45 | 47 (28.3) | 160 (31.4) | 207 (30.7) |
| | >=45 and <55 | 44 (26.5) | 153 (30.1) | 197 (29.2) |
| | >=55 and <65 | 30 (18.1) | 64 (12.6) | 94 (13.9) |
| | >=65 | 7 (4.2) | 27 (5.3) | 34 (5.0) |
| Sex n (%) | F | 39 (23.5) | 116 (22.8) | 155 (23.0) |
| | M | 127 (76.5) | 393 (77.2) | 520 (77.0) |
| Race n (%) | ASIAN | | 1 (0.2) | 1 (0.1) |
| | BLACK | | 1 (0.2) | 1 (0.1) |
| | CAUCASIAN | 165 (99.4) | 506 (99.4) | 671 (99.4) |
| | OTHER | 1 (0.6) | 1 (0.2) | 2 (0.3) |

TABLE 5

Number of patients in efficacy analysis

| Study | Population | Placebo | Nalmefene |
|---|---|---|---|
| 12014A | Total population | 289 | 290 |
| | High DRL at baseline | 230 | 222 |
| | Total excl. ERs | 231 | 246 |
| | High DRL at baseline & randomisation | 167 | 171 |
| 12023A | Total population | 326 | 329 |
| | High DRL at baseline | 247 | 265 |
| | Total excl. ERs | 221 | 216 |
| | High DRL at baseline & randomisation | 155 | 148 |
| 12013A | Total population | 137 | 415 |
| | High DRL at baseline | 88 | 252 |
| | Total excl. ERs | 79 | 258 |
| | High DRL at baseline & randomisation | 42 | 141 |

The efficacy of nalmefene was measured using two co-primary endpoints: the change in the monthly number of heavy drinking days (HDDs) and the change in the mean daily total alcohol consumption (TAC) per month (=28 days). A HDD was defined as a day with a consumption ≥60 g alcohol for men and a ≥40 g for women. Data obtained at month 6 are listed in Table 6 below. The change in HDD and TAC over time in patients treated with nalmefene or placebo is furthermore reflected in FIGS. 1-12.

TABLE 6

Results (Mixed model repeated measures (MMRM) analysis) at Month 6.

| Study | Endpoint | Population | Mean difference to placebo in the change from baseline to month 6 | p-value |
|---|---|---|---|---|
| 12014A | HDD | Total population | −2.3 days/month | 0.002 |
| | | High DRL at baseline | −2.6 days/month | 0.006 |
| | | Total excl. ERs | −3.1 days/month | <0.001 |
| | | High DRL at baseline & randomisation | −3.7 days/month | 0.001 |
| | TAC | Total population | −11.0 g/day | <0.001 |
| | | High DIRL at baseline | −12.2 g/day | <0.001 |
| | | Total excl. ERs | −14.5 g/day | <0.001 |
| | | High DRL at baseline & randomisation | −18.3 g/day | <0.001 |
| 12023A | HDD | Total population | −1.7 days/month | 0.012 |
| | | High DRL at baseline | −2.1 days/month | 0.010 |
| | | Total excl. ERs | −2.0 days/month | 0.012 |
| | | High DRL at baseline & randomisation | −2.7 days/month | 0.025 |
| | TAC | Total population | −5.0 g/day | 0.088 |
| | | High DRL at baseline | −6.6 g/day | 0.062 |
| | | Total excl. ERs | −7.0 g/day | 0.037 |
| | | High DRL at baseline & randomisation | −10.3 g/day | 0.040 |
| 12013A | HDD | Total population | −0.9 days/month | 0.160 |
| | | High DRL at baseline | −1.1 days/month | 0.253 |
| | | Total excl. ERs | −1.4 days/month | 0.082 |
| | | High DRL at baseline & randomisation | −2.6 days/month | 0.071 |
| | TAC | Total population | −3.5 g/day | 0.232 |
| | | High DRL at baseline | −5.6 g/day | 0.219 |
| | | Total excl. ERs | −7.9 g/day | 0.036 |
| | | High DRL at baseline & randomisation | −15.3 g/day | 0.031 |

Table 6 indicates that in all three studies the difference between nalmefene and placebo measured in HDDs and TAC was more pronounced in the group of patients with High DRL at baseline than in the total study population.

Table 6 also indicates that in all three studies the difference between nalmefene and placebo measured in HDDs and TAC was more pronounced in the group of patients excluding ERs than in the total study population.

Finally, table 6 clearly indicates that in all three studies the difference between nalmefene and placebo measured in HDDs and TAC was more pronounced in the group of patients with High DRL at baseline and randomization than in the total study population.

The invention claimed is:

1. A method for reducing alcohol consumption in a patient with alcohol dependence comprising:
    a) identifying a patient with alcohol dependence;
        i. wherein said patient has a drinking risk level corresponding to a mean daily consumption of >60 g of alcohol for men and >40 g of alcohol for women; and
        ii. wherein said patient maintains said drinking risk level after an observation period following initial assessment; and
    b) administering a therapeutically effective amount of nalmefene to said patient.

2. The method of claim 1, wherein nalmefene is administered on each day the patient perceives a risk of drinking alcohol.

3. The method of claim 1, wherein the nalmefene is administered to said patient as needed.

4. The method of claim 3, wherein said nalmefene is administered on each day the patient perceives a risk of drinking alcohol.

5. The method of claim 4, wherein nalmefene is administered 1-2 hours prior to the anticipated time of drinking.

6. The method of claim 1, further comprising excluding patients who have reduced their alcohol consumption during the observation period to a level below >60 g of alcohol for men and >40 g and alcohol for women.

7. The method of claim 1, wherein nalmefene is administered 1-2 hours prior to anticipated time of drinking.

8. The method of claim 1, wherein said drinking risk level in step (i) is assessed by calculating mean daily alcohol consumption over at least one week preceding assessment.

9. The method of claim 8, wherein said drinking risk level in step (i) is assessed by calculating mean daily alcohol consumption over at least 2 weeks preceding assessment.

10. The method of claim 1, wherein nalmefene is administered in a dose of about 10-20 mg.

11. The method of claim 10, wherein nalmefene is administered in a dose of about 18 mg.

12. The method of claim 1, wherein nalmefene is administered for a treatment period of 6-12 months.

13. The method of claim 1, wherein nalmefene is administered as a pharmaceutically acceptable salt.

14. The method of claim 13, wherein nalmefene is administered as the hydrochloride dihydrate.

15. The method of claim 1, wherein nalmefene is administered in combination with a further active ingredient.

16. The method of claim 1, wherein said observation period following initial assessment is about 1-2 weeks.

17. The method of claim 16, wherein said observation period following initial assessment is about 2 weeks.

18. A method for reducing alcohol consumption in a patient with alcohol dependence comprising, administering a therapeutically effective amount of nalmefene to the patient, wherein the patient maintains a drinking risk level corresponding to a mean daily consumption of >60 g of alcohol for men and >40 g of alcohol for women after an observation period following initial assessment.

19. The method of claim 18, further comprising excluding patients who have reduced their alcohol consumption during the observation period to a level below >60 g of alcohol for men and >40 g and alcohol for women.

20. The method of claim 18, wherein prior to the initial assessment the patient has a drinking risk level corresponding to a mean daily consumption of >60 g of alcohol for men and >40 g of alcohol for women.

21. The method of claim 18, wherein nalmefene is administered on each day the patient perceives a risk of drinking alcohol.

22. The method of claim 18, wherein the nalmefene is administered to said patient as needed.

23. The method of claim 22, wherein said nalmefene is administered on each day the patient perceives a risk of drinking alcohol.

24. The method of claim 18, wherein nalmefene is administered 1-2 hours prior to anticipated time of drinking.

25. The method of claim 18, wherein said drinking risk level in the initial assessment is determined by calculating mean daily alcohol consumption over at least one week preceding assessment.

26. The method of claim 25, wherein said drinking risk level in the initial assessment is determined by calculating mean daily alcohol consumption over at least two weeks preceding assessment.

27. The method of claim 18, wherein nalmefene is administered in a dose of about 10-20 mg.

28. The method of claim 27, wherein nalmefene is administered in a dose of about 18 mg.

29. The method of claim 18, wherein nalmefene is administered for a treatment period of 6-12 months.

30. The method of claim 18, wherein nalmefene is administered as a pharmaceutically acceptable salt.

31. The method of claim 30, wherein nalmefene is administered as the hydrochloride dihydrate.

32. The method of claim 18, wherein nalmefene is administered in combination with a further active ingredient.

33. The method of claim 18, wherein said observation period following initial assessment is about 1-2 weeks.

34. The method of claim 33, wherein said observation period following initial assessment is about 2 weeks.

35. The method of claim 23, wherein nalmefene is administered 1-2 hours prior to the anticipated time of drinking.

\* \* \* \* \*